United States Patent
Albert et al.

(10) Patent No.: US 11,026,722 B2
(45) Date of Patent: Jun. 8, 2021

(54) ORTHOPEDIC TETHERED IMPLANTS AND SYSTEM

(71) Applicant: OrthoPediatrics Corp., Warsaw, IN (US)

(72) Inventors: Michael Albert, Dayton, OH (US);
Stuart Lindquist, Apex, NC (US);
Randy Roof, Matthews, NC (US);
John Kapitan, Leicester, NC (US)

(73) Assignee: OrthoPediatrics Corp., Warsaw, IN (US)

( * ) Notice: Subject to any disclaimer, the term of this patent is extended or adjusted under 35 U.S.C. 154(b) by 124 days.

(21) Appl. No.: 15/660,542

(22) Filed: Jul. 26, 2017

(65) Prior Publication Data

US 2018/0014857 A1    Jan. 18, 2018
US 2021/0077153 A9    Mar. 18, 2021

Related U.S. Application Data

(60) Continuation-in-part of application No. 15/058,582, filed on Mar. 2, 2016, now Pat. No. 9,770,268, and a
(Continued)

(51) Int. Cl.
*A61B 17/70* (2006.01)
*A61B 17/88* (2006.01)
(Continued)

(52) U.S. Cl.
CPC ...... *A61B 17/7034* (2013.01); *A61B 17/7032* (2013.01); *A61B 17/7049* (2013.01);
(Continued)

(58) Field of Classification Search
CPC ............ A61B 17/7022; A61B 17/7053; A61B 17/842; A61B 17/86
(Continued)

(56) References Cited

U.S. PATENT DOCUMENTS 902,040 A    10/1908    Wyckoff
2,001,091 A    5/1935    Carlson
(Continued)

FOREIGN PATENT DOCUMENTS

AU    2008289395 A1    2/2009
DE    4021246 A1    1/1992
(Continued)

*Primary Examiner* — Eduardo C Robert
*Assistant Examiner* — Christina Negrellirodriguez
(74) *Attorney, Agent, or Firm* — John V. Daniluck; Gerald W. Roberts; Dentons Bingham Greenebaum LLP

(57) ABSTRACT

A clamp assembly for orthopedic use having a housing that includes a top surface, a recess, a distal base and a bottom surface, the recess defining a longitudinal axis and extending through the housing from the top surface through the distal base and toward the bottom surface, and at least two through slots, each one of being disposed at a bottom or a side a surface of the housing. The assembly including a securement assembly positionable within the recess in a co-axial relationship to a mating surface on the recess, and a band sized for travel along a predetermined path defined in part by the through slots in the housing, wherein at least one of the through slots is a starting point for travel of the band along the predetermined path.

14 Claims, 25 Drawing Sheets

Related U.S. Application Data continuation-in-part of application No. 14/746,226, filed on Jun. 22, 2015, now Pat. No. 9,770,267, said application No. 15/058,582 is a division of application No. 14/746,226, filed on Jun. 22, 2015, now Pat. No. 9,770,267, which is a division of application No. 13/618,724, filed on Sep. 14, 2012, now Pat. No. 9,173,685.

(60) Provisional application No. 62/366,866, filed on Jul. 26, 2016, provisional application No. 61/534,453, filed on Sep. 14, 2011, provisional application No. 61/595,296, filed on Feb. 6, 2012.

(51) Int. Cl.
*A61B 17/86* (2006.01)
*A61B 17/56* (2006.01)

(52) U.S. Cl.
CPC ...... *A61B 17/7053* (2013.01); *A61B 17/7076* (2013.01); *A61B 17/8605* (2013.01); *A61B 17/8685* (2013.01); *A61B 17/8869* (2013.01); *A61B 17/56* (2013.01); *A61B 17/7035* (2013.01); *A61B 17/7077* (2013.01)

(58) Field of Classification Search
USPC ......... 606/74, 103, 105, 138–140, 228, 277, 606/279, 324
See application file for complete search history.

(56) References Cited

U.S. PATENT DOCUMENTS

| | | | |
|---|---|---|---|
| 2,014,091 A | 9/1935 | Shepard | |
| 2,049,361 A | 7/1936 | Ericsson | |
| 2,093,145 A | 9/1937 | Carruthers | |
| 4,037,603 A | 7/1977 | Wendorff | |
| 4,443,915 A | 4/1984 | Niemeyer | |
| 4,557,259 A | 12/1985 | Wu | |
| 4,570,618 A | 2/1986 | Wu | |
| 4,716,630 A | 1/1988 | Skyba | |
| 5,092,866 A | 3/1992 | Breard et al. | |
| 5,133,111 A | 7/1992 | Brown | |
| 5,161,351 A | 11/1992 | Woodruff | |
| 5,291,638 A | 3/1994 | Huang | |
| 5,356,412 A | 10/1994 | Golds et al. | |
| 5,380,326 A | 1/1995 | Lin | |
| 5,395,374 A | 3/1995 | Miller et al. | |
| 5,403,314 A | 4/1995 | Currier | |
| 5,549,607 A | 8/1996 | Olson et al. | |
| 5,669,917 A | 9/1997 | Sauer et al. | |
| 5,702,399 A | 12/1997 | Kilpela et al. | |
| 5,772,663 A | 6/1998 | Whiteside et al. | |
| RE36,221 E | 6/1999 | Breard et al. | |
| 5,920,963 A | 7/1999 | Chou | |
| 5,935,133 A | 8/1999 | Wagner et al. | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,228,096 B1 | 5/2001 | Marchand | |
| 6,277,120 B1 | 8/2001 | Lawson | |
| 6,290,700 B1 | 9/2001 | Schmotzer | |
| 6,296,643 B1 | 10/2001 | Hopf et al. | |
| 6,325,802 B1 | 12/2001 | Frigg | |
| 6,391,030 B1 | 5/2002 | Wagner et al. | |
| 6,415,480 B1 | 7/2002 | Kane et al. | |
| 6,436,099 B1 | 8/2002 | Drewry et al. | |
| 6,514,255 B1 | 2/2003 | Ferree | |
| 6,641,584 B2 | 11/2003 | Hashimoto et al. | |
| 6,682,533 B1 | 1/2004 | Dinsdale et al. | |
| 6,689,140 B2 | 2/2004 | Cohen | |
| 7,207,090 B2 | 4/2007 | Mattchen | |
| 7,255,701 B2 | 8/2007 | Allen et al. | |
| 7,334,301 B2 | 2/2008 | Huang | |
| 7,367,978 B2 | 5/2008 | Drewry et al. | |
| 7,444,720 B2 | 11/2008 | Huang | |
| 7,468,067 B2 | 12/2008 | Licata et al. | |
| 7,524,324 B2 | 4/2009 | Winslow et al. | |
| 7,824,430 B2 | 11/2010 | Allard et al. | |
| 7,901,436 B2 | 3/2011 | Baccelli | |
| 8,257,367 B2 | 9/2012 | Bryant et al. | |
| 8,323,294 B2 | 12/2012 | Mickiewicz et al. | |
| 8,430,918 B2 | 4/2013 | Baccelli et al. | |
| 8,465,527 B2 | 6/2013 | Clement | |
| 8,469,966 B2 | 6/2013 | Allen et al. | |
| 8,870,869 B2 | 10/2014 | Meunier et al. | |
| 8,926,668 B2 | 1/2015 | Douget | |
| 9,039,711 B2 | 5/2015 | Mickiewicz et al. | |
| 9,101,425 B2 | 8/2015 | Douget et al. | |
| 9,173,685 B2 | 11/2015 | Lindquist et al. | |
| 9,204,902 B2 | 12/2015 | Belliard et al. | |
| 9,204,903 B2 | 12/2015 | Belliard et al. | |
| 9,216,047 B2 | 12/2015 | Bryant | |
| 9,314,275 B2 | 4/2016 | Clement | |
| 9,345,518 B2 | 5/2016 | Larroque-Lahitette | |
| 9,358,054 B2 | 6/2016 | Garcia | |
| 9,393,051 B2 | 7/2016 | Baccelli | |
| 9,393,063 B2 | 7/2016 | Mickiewicz | |
| 9,433,441 B2 | 9/2016 | George | |
| 9,492,165 B2 | 11/2016 | Serhan et al. | |
| 9,492,207 B2 | 11/2016 | Baccelli et al. | |
| 2001/0034522 A1 | 10/2001 | Frigg | |
| 2002/0072753 A1 | 6/2002 | Cohen | |
| 2002/0116013 A1 | 8/2002 | Gleason et al. | |
| 2004/0138666 A1 | 7/2004 | Molz, IV et al. | |
| 2006/0036255 A1 | 2/2006 | Pond et al. | |
| 2006/0217726 A1 | 9/2006 | Maxy et al. | |
| 2006/0229623 A1 | 10/2006 | Bonutti et al. | |
| 2007/0072493 A1 | 3/2007 | Soumac et al. | |
| 2007/0088362 A1 | 4/2007 | Bonutti et al. | |
| 2007/0167949 A1 | 7/2007 | Altarac et al. | |
| 2007/0203491 A1 | 8/2007 | Pasquet et al. | |
| 2007/0226961 A1 | 10/2007 | Anderson et al. | |
| 2007/0288026 A1 | 12/2007 | Shluzas | |
| 2008/0033557 A1 | 2/2008 | Pasquet et al. | |
| 2008/0058818 A1 | 3/2008 | Schwab | |
| 2008/0140122 A1 | 6/2008 | Bethell | |
| 2008/0255576 A1 | 10/2008 | Protopsaltis | |
| 2008/0262551 A1 | 10/2008 | Rice et al. | |
| 2008/0275469 A1 | 11/2008 | Fanton et al. | |
| 2009/0054902 A1 | 2/2009 | Mickiewicz et al. | |
| 2009/0105715 A1* | 4/2009 | Belliard ............ | A61B 17/7053 606/103 |
| 2009/0131982 A1 | 5/2009 | Schwab | |
| 2009/0138048 A1 | 5/2009 | Baccelli et al. | |
| 2009/0198273 A1 | 8/2009 | Zhang et al. | |
| 2009/0281575 A1 | 11/2009 | Carls et al. | |
| 2009/0292317 A1 | 11/2009 | Belliard | |
| 2010/0094302 A1 | 4/2010 | Pool et al. | |
| 2010/0106195 A1 | 4/2010 | Sefton et al. | |
| 2010/0249845 A1 | 9/2010 | Meunier et al. | |
| 2010/0275420 A1 | 11/2010 | Huang | |
| 2011/0112581 A1 | 5/2011 | Clement | |
| 2011/0152950 A1 | 6/2011 | Baccelli | |
| 2011/0218573 A1 | 9/2011 | Ferree | |
| 2011/0295323 A1 | 12/2011 | Hudgins et al. | |
| 2011/0301644 A1 | 12/2011 | Belliard | |
| 2012/0130373 A1* | 5/2012 | Larroque-Lahitette ..................... | A61B 17/7001 606/74 |
| 2012/0143207 A1 | 6/2012 | Belliard et al. | |
| 2013/0023878 A1 | 1/2013 | Belliard et al. | |
| 2013/0035726 A1 | 2/2013 | Nguyen et al. | |
| 2013/0041410 A1 | 2/2013 | Hestad et al. | |
| 2013/0060287 A1 | 3/2013 | Mickiewicz et al. | |
| 2013/0072983 A1 | 3/2013 | Lindquist et al. | |
| 2013/0245691 A1 | 9/2013 | Hutton et al. | |
| 2013/0261668 A1 | 10/2013 | Douget et al. | |
| 2013/0268011 A1 | 10/2013 | Rezach et al. | |
| 2013/0325070 A1 | 12/2013 | Larroque-Lahitette et al. | |
| 2014/0018808 A1 | 1/2014 | Allen et al. | |

(56) References Cited

U.S. PATENT DOCUMENTS

| | | |
|---|---|---|
| 2014/0066987 A1 | 3/2014 | Hestad et al. |
| 2014/0114356 A1 | 4/2014 | Le Couedic et al. |
| 2014/0257398 A1 | 9/2014 | Baccelli et al. |
| 2014/0257400 A1 | 9/2014 | George et al. |
| 2014/0257401 A1 | 9/2014 | George et al. |
| 2014/0277149 A1 | 9/2014 | Rooney et al. |
| 2014/0277207 A1 | 9/2014 | Baccelli et al. |
| 2015/0173739 A1 | 6/2015 | Rodriguez et al. |
| 2015/0223845 A1 | 8/2015 | Larroque-Lahitette |
| 2015/0297271 A1 | 10/2015 | Finley |
| 2015/0313657 A1 | 11/2015 | Belliard |
| 2015/0342654 A1 | 12/2015 | Gephart |
| 2016/0038194 A1 | 2/2016 | Belliard et al. |
| 2016/0089131 A1 | 3/2016 | Wade |
| 2016/0183983 A1 | 6/2016 | Heflin |
| 2016/0296265 A1 | 10/2016 | Mickiewicz et al. |
| 2016/0324547 A1 | 11/2016 | Miller et al. |
| 2017/0086894 A1 | 3/2017 | Garcia et al. |

FOREIGN PATENT DOCUMENTS

| | | |
|---|---|---|
| DE | 19716504 A1 | 12/1998 |
| EP | 0780096 A1 | 6/1997 |
| EP | 09828603 A1 | 7/1999 |
| EP | 1205152 A1 | 5/2002 |
| EP | 2197370 A1 | 6/2010 |
| FR | 820187 A | 11/1937 |
| FR | 2369825 A | 6/1978 |
| FR | 2656214 A1 | 6/1991 |
| FR | 2704745 A1 | 11/1994 |
| FR | 2900561 A1 | 11/2007 |
| GB | 2207055 A | 1/1989 |
| WO | WO9849960 A1 | 11/1998 |
| WO | WO9953855 A1 | 10/1999 |
| WO | WO0209604 A1 | 2/2002 |
| WO | 2006/106268 A1 | 10/2006 |
| WO | WO2009025966 A1 | 2/2009 |
| WO | WO2009130276 A1 | 10/2009 |
| WO | 2011/012690 A1 | 2/2011 |
| WO | WO2015167920 A1 | 11/2015 |

\* cited by examiner

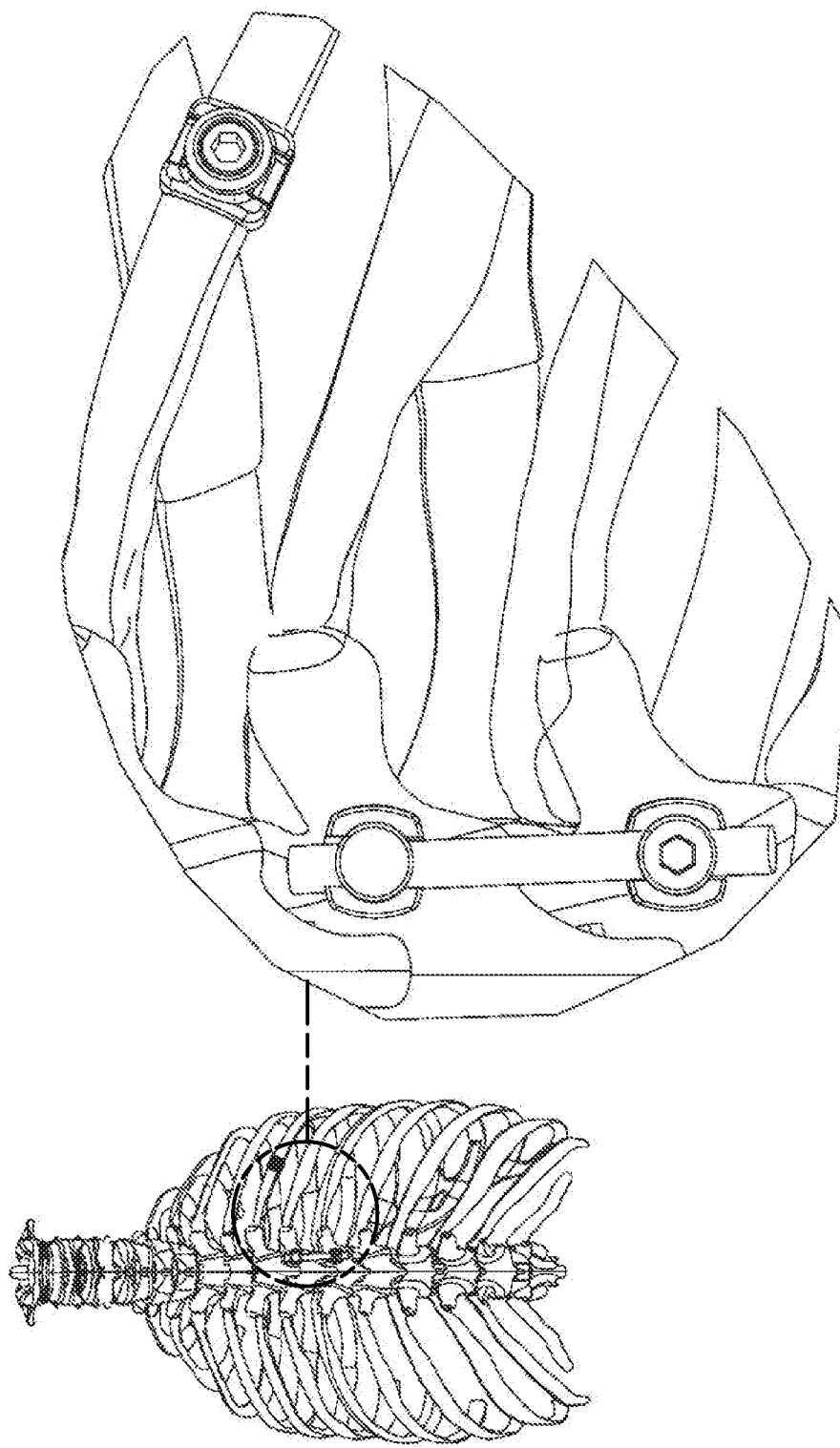
Figure A1

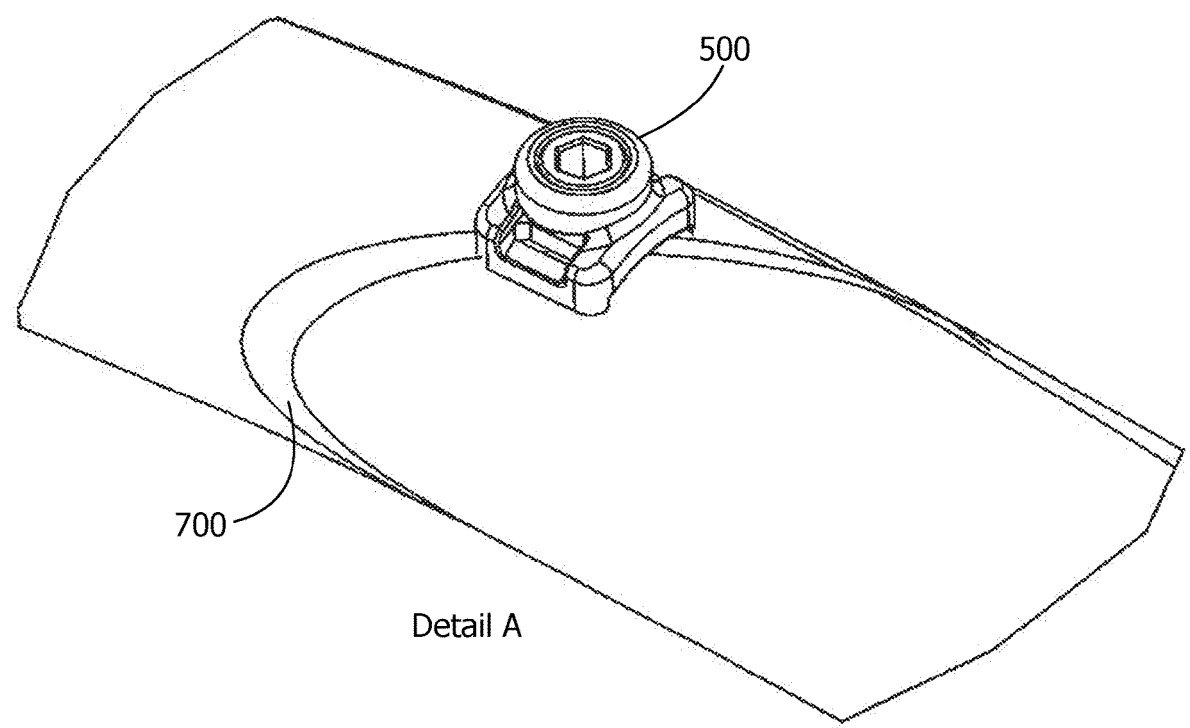
Detail A
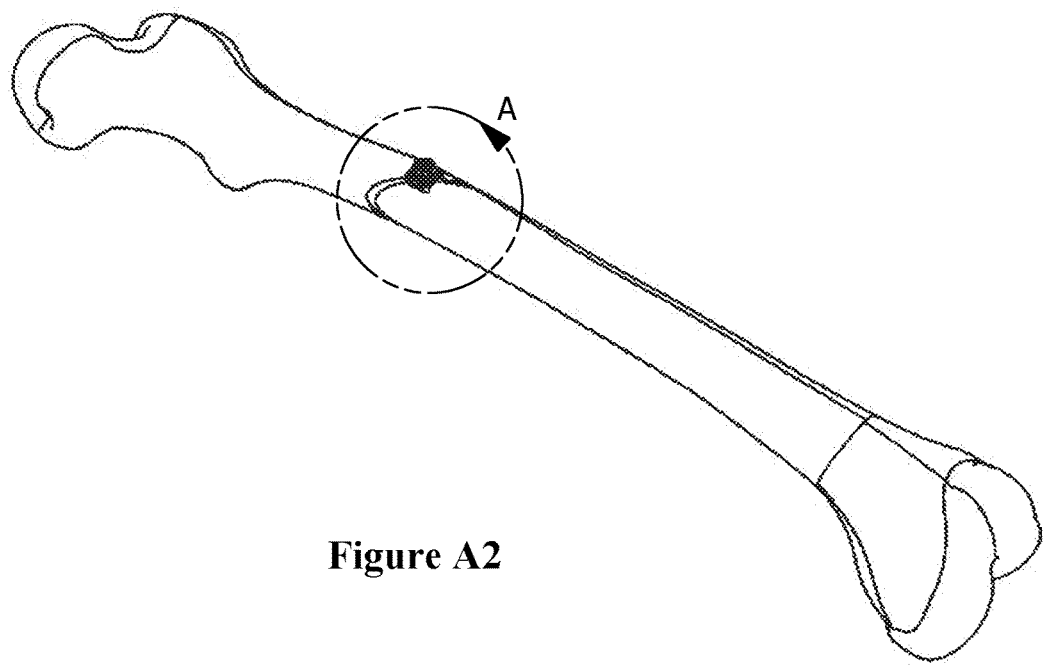
Figure A2

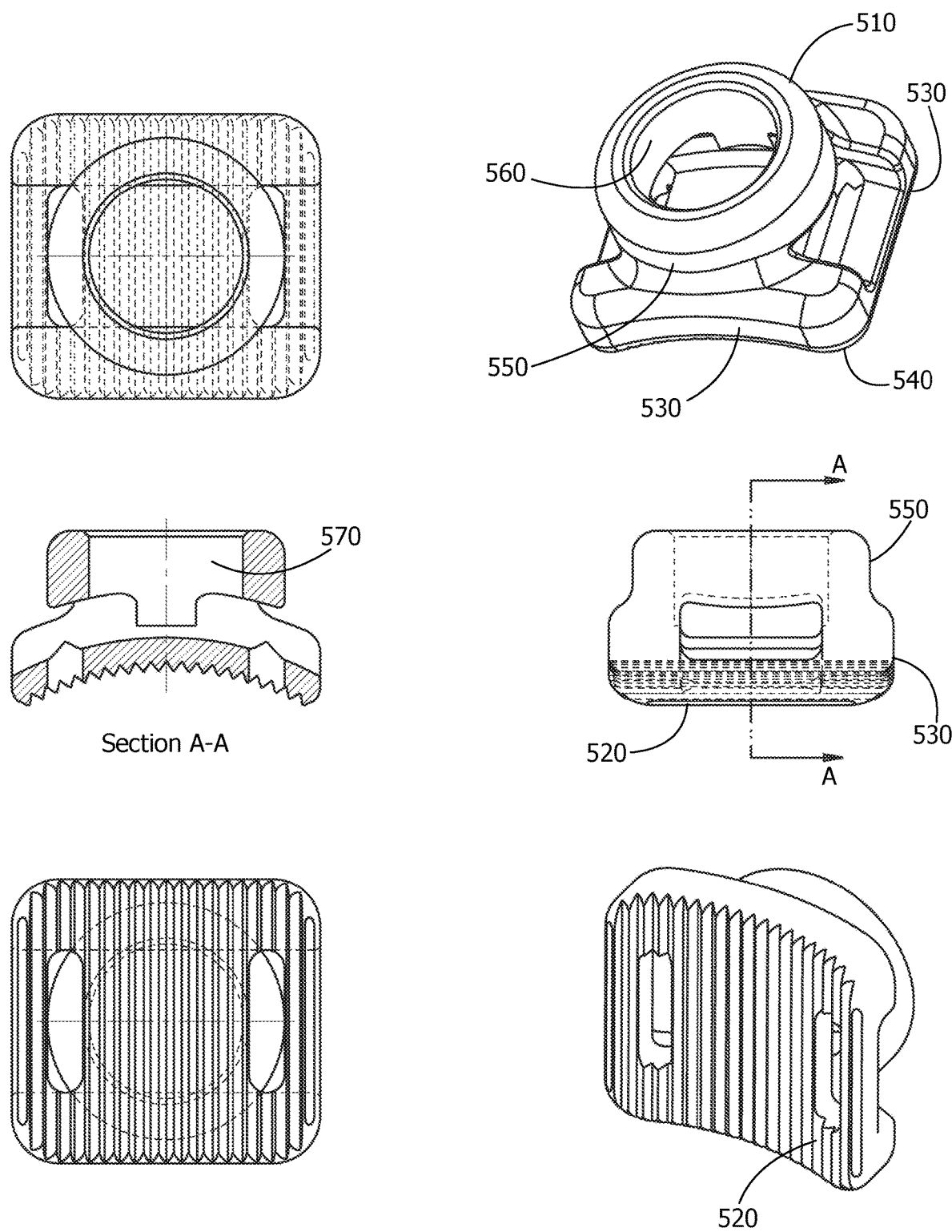
Figure A3

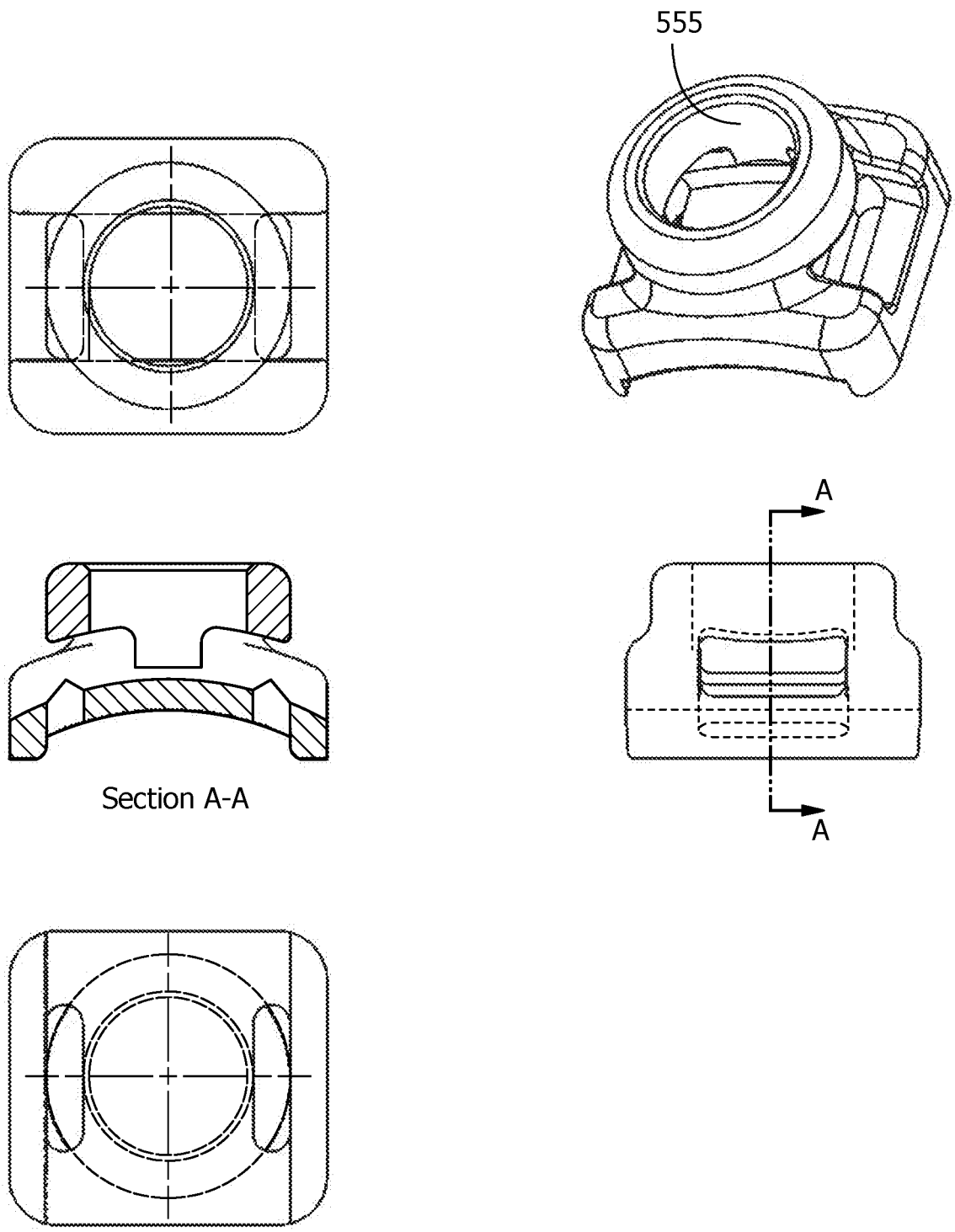
Figure A4

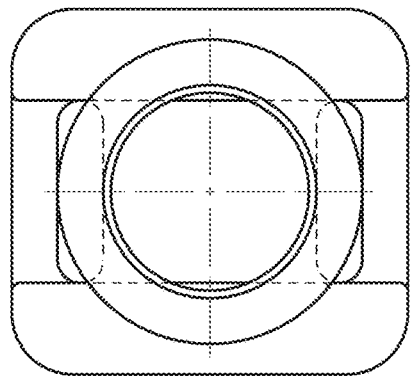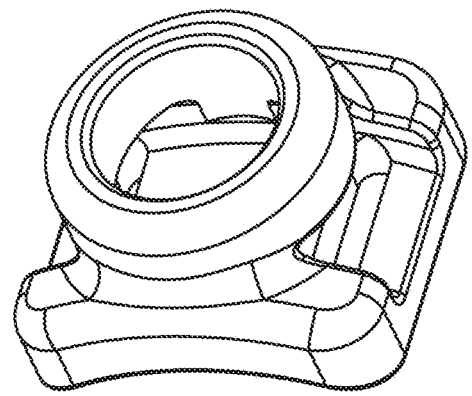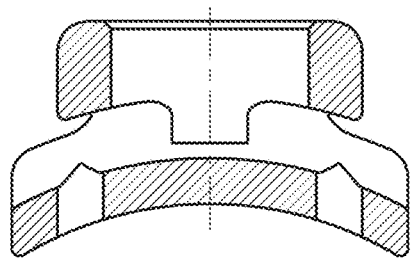
SECTION A-A
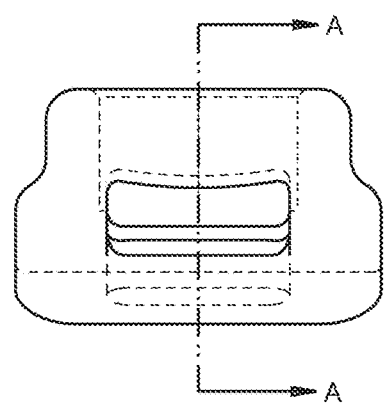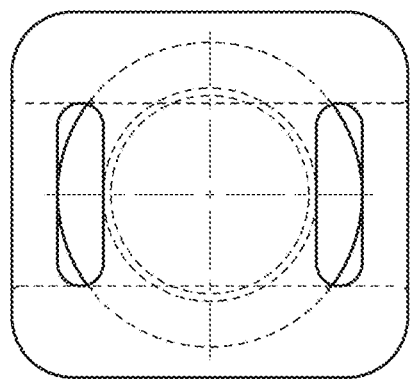
Figure A5

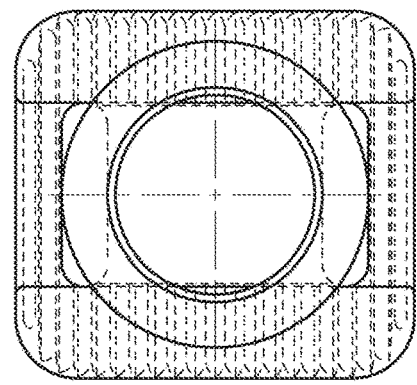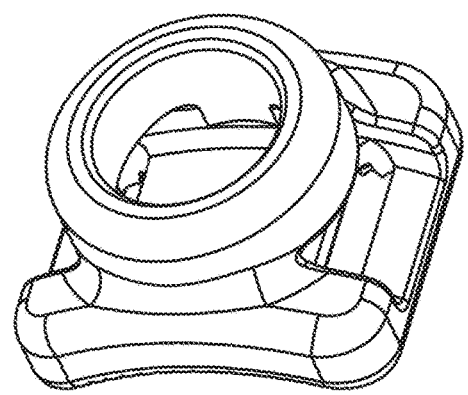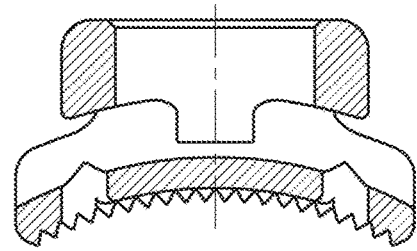
Section A-A
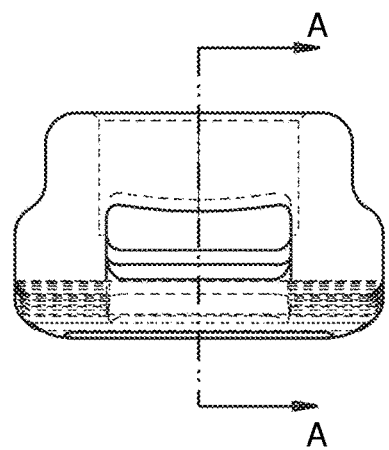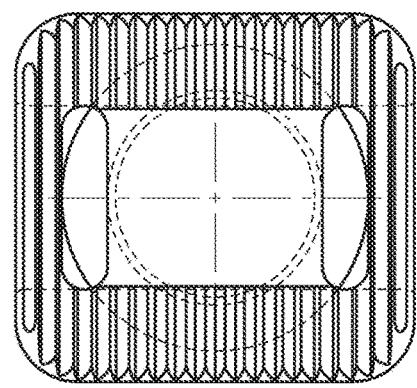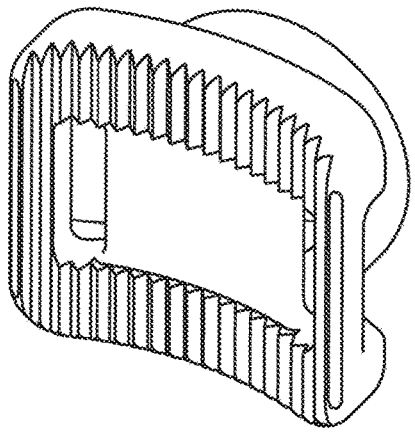
Figure A6

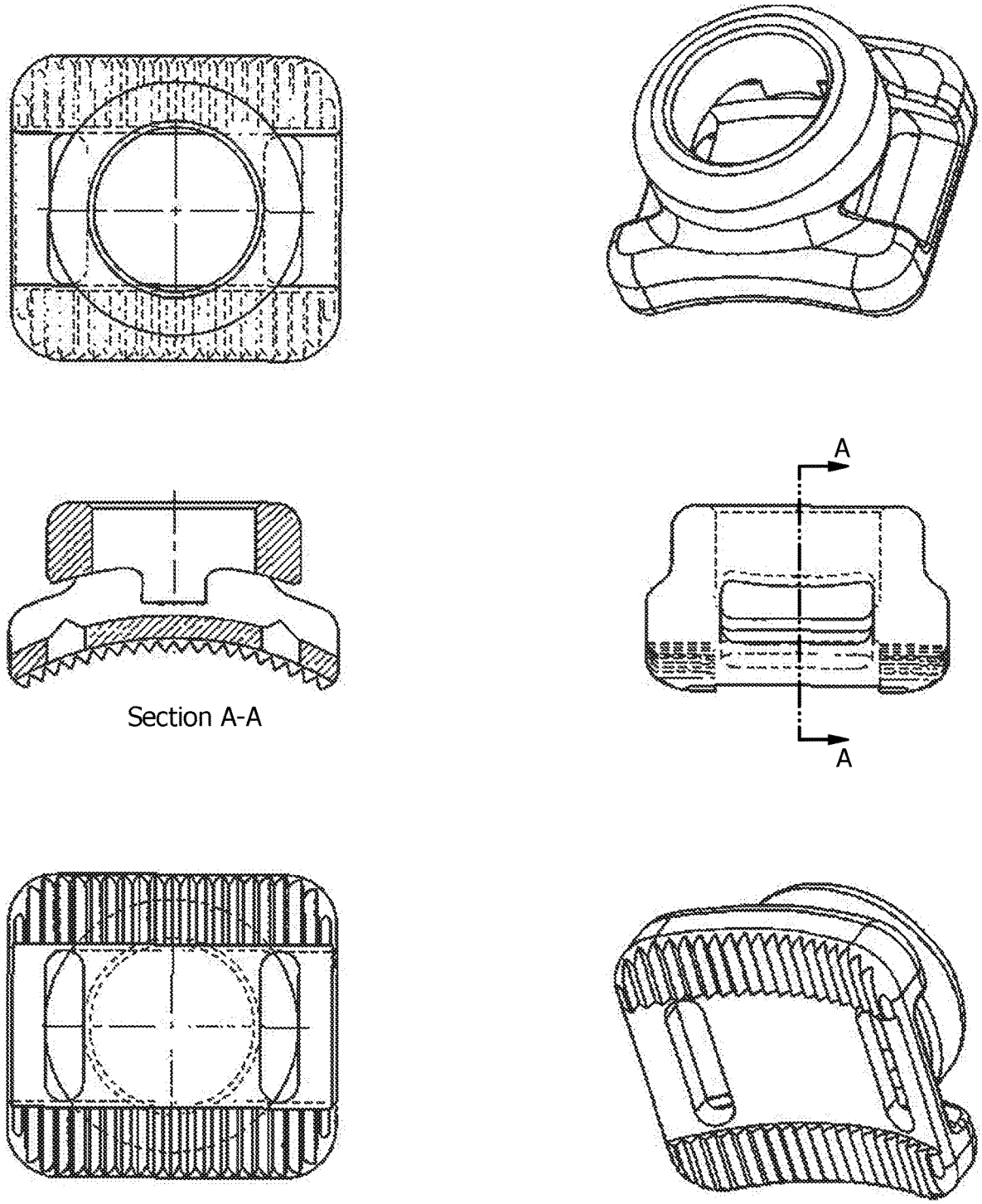
Figure A7

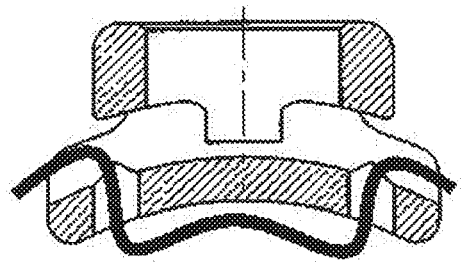
Section A-A
A1
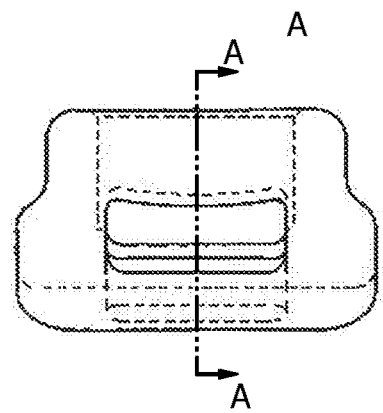
A2
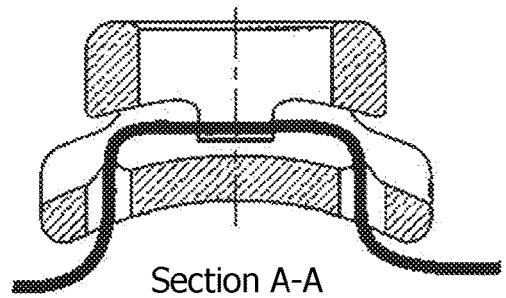
Section A-A
B1
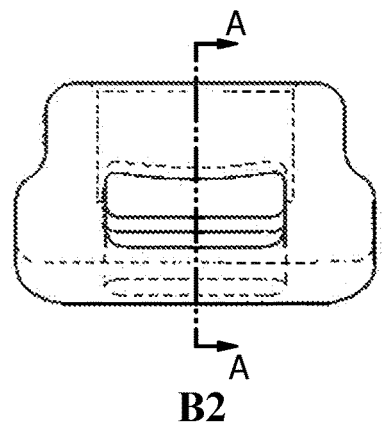
B2
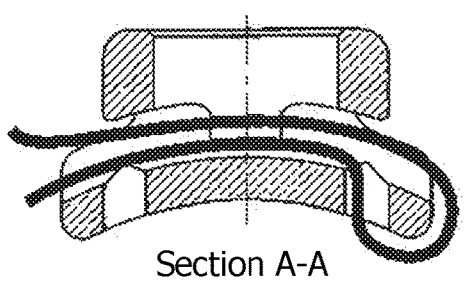
Section A-A
C1
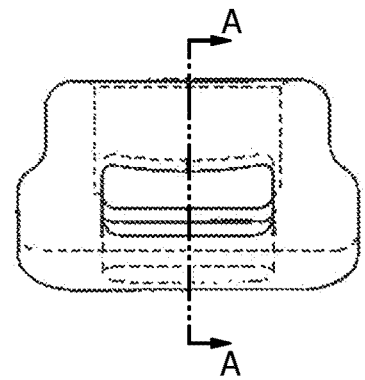
C2
Figure A8

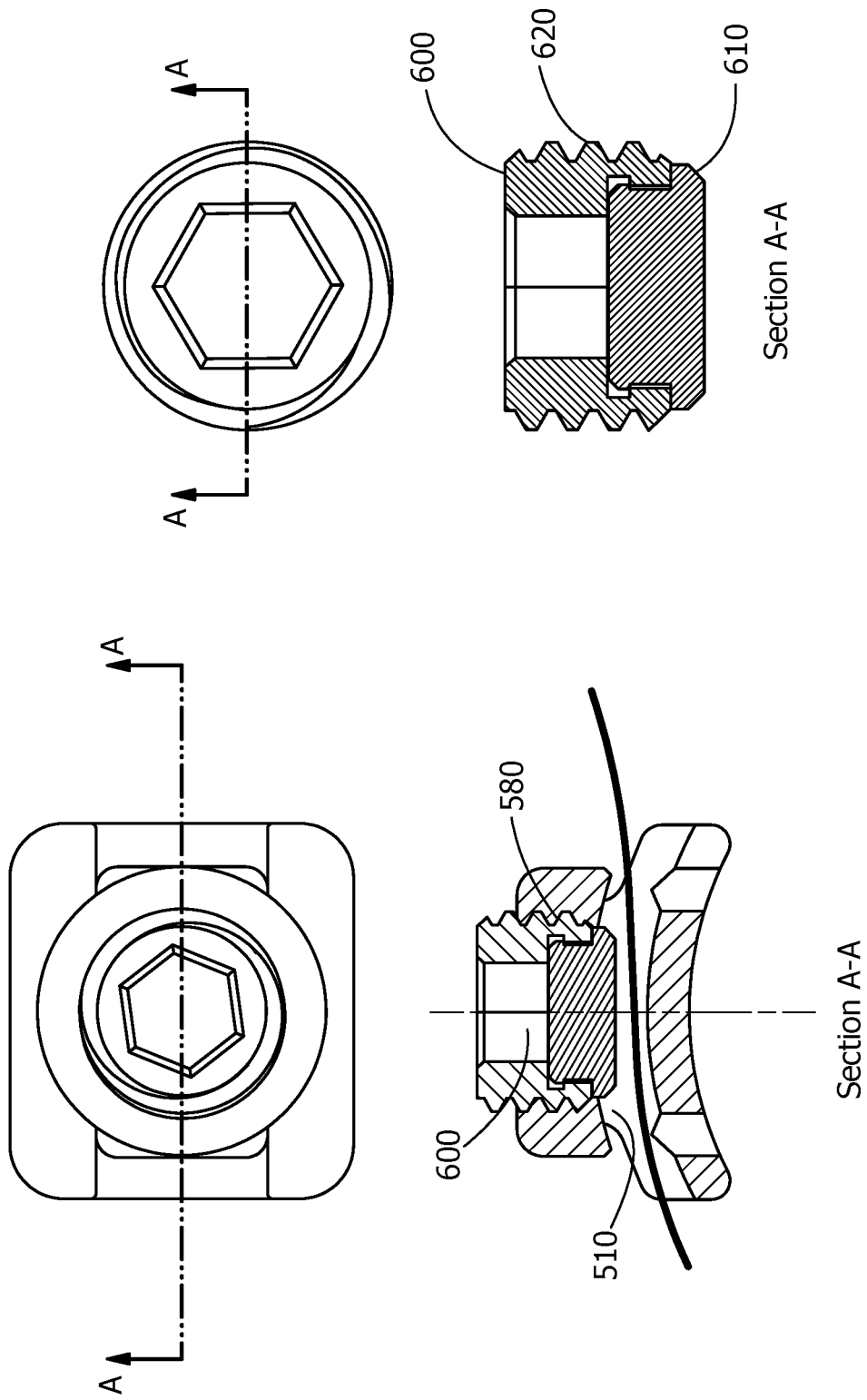
Figure A9

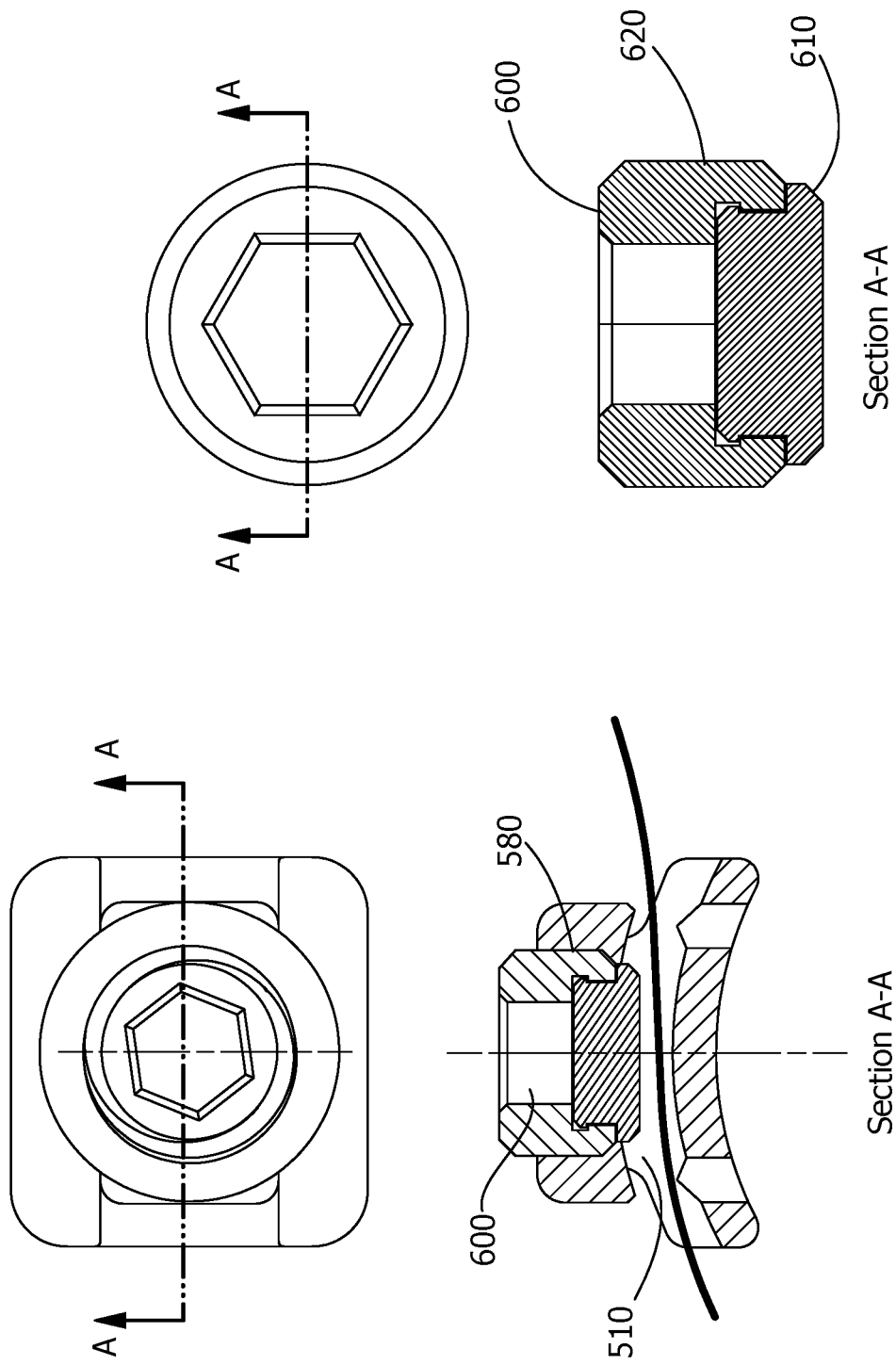
Figure A10

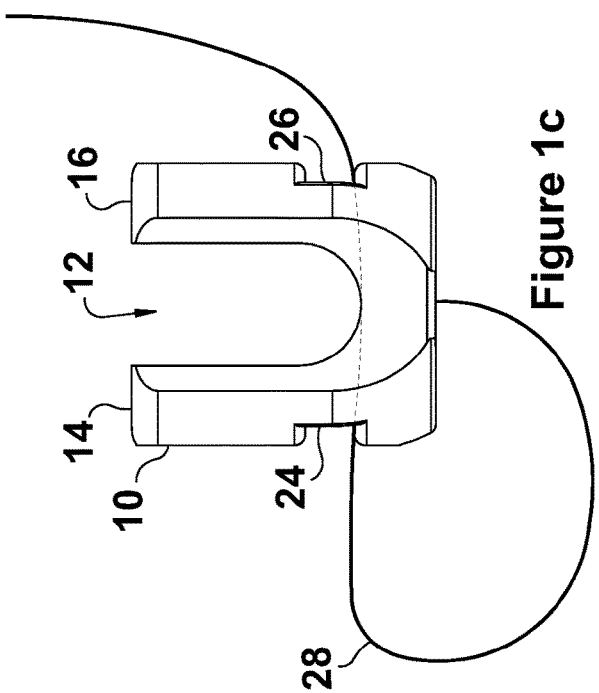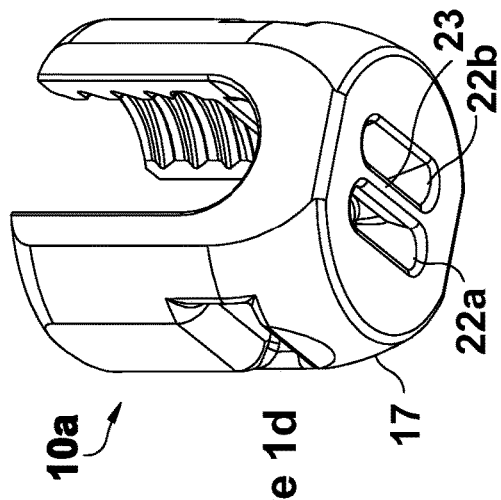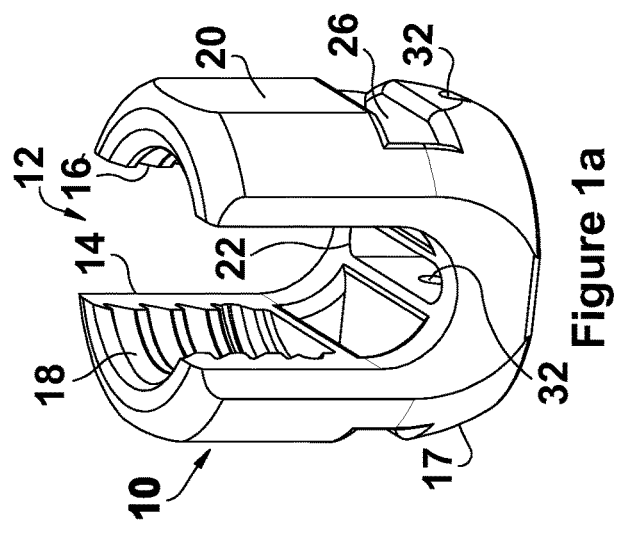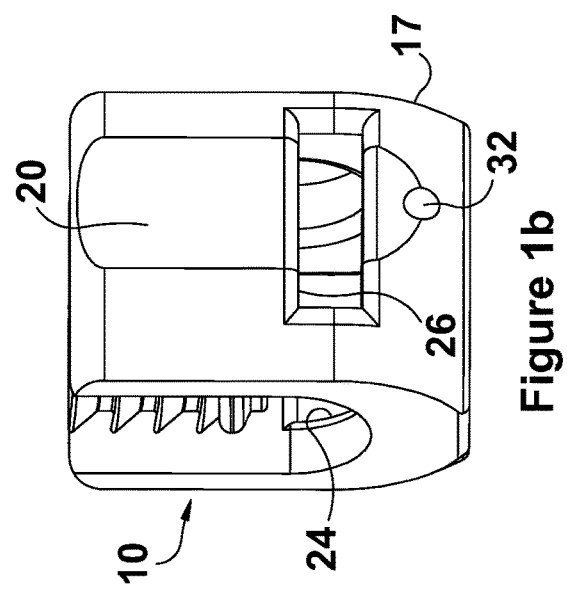
Figure 1a
Figure 1b
Figure 1c
Figure 1d

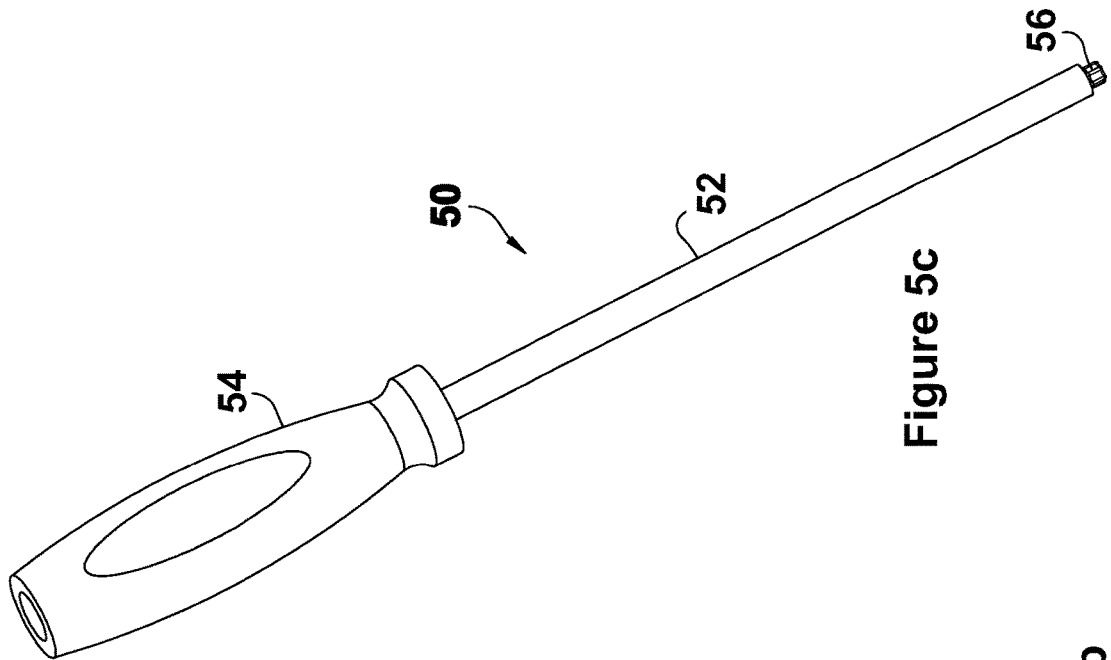
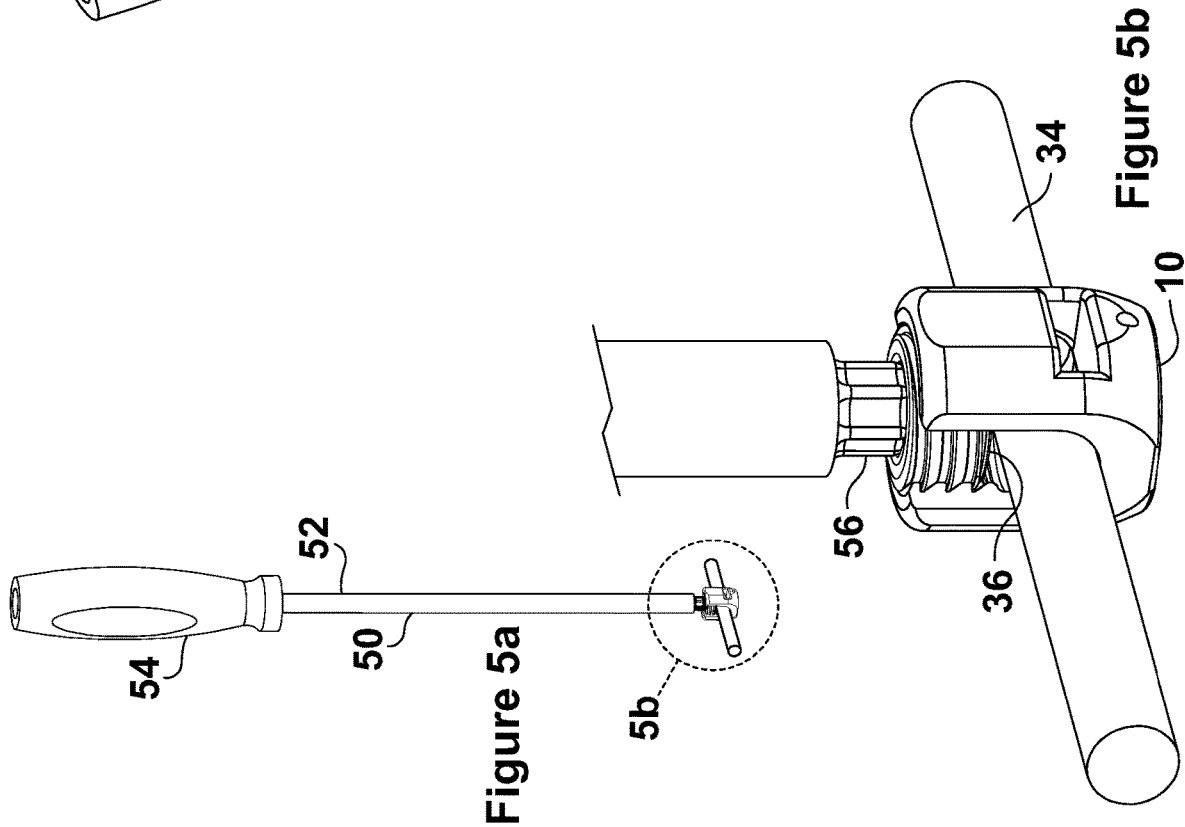

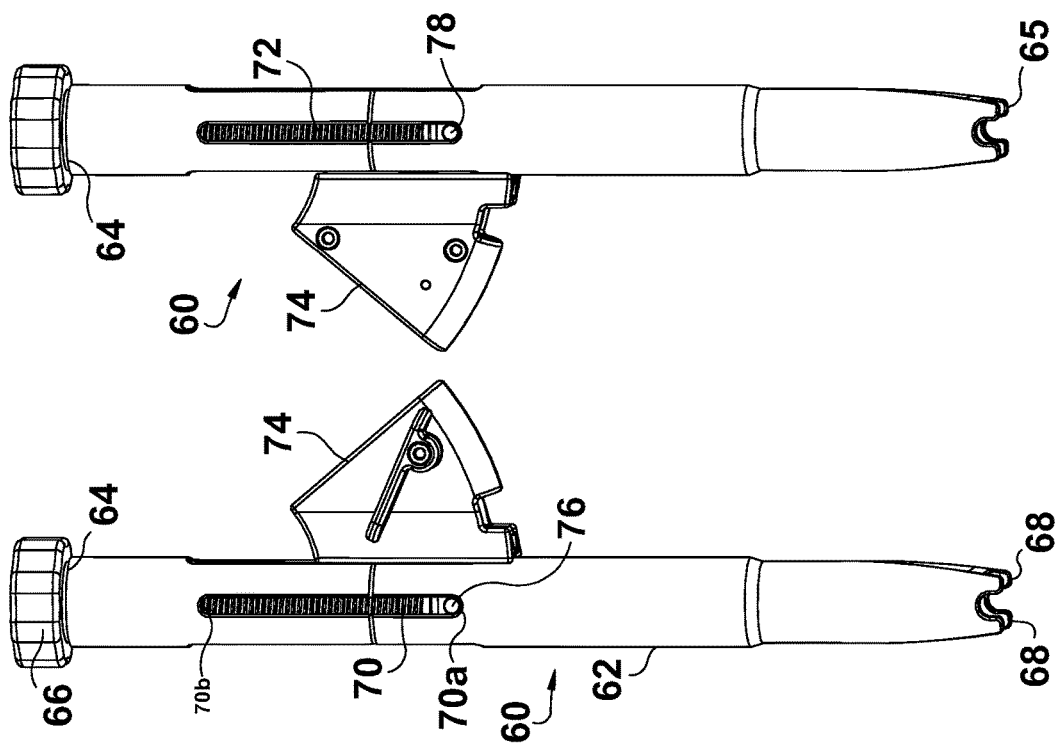
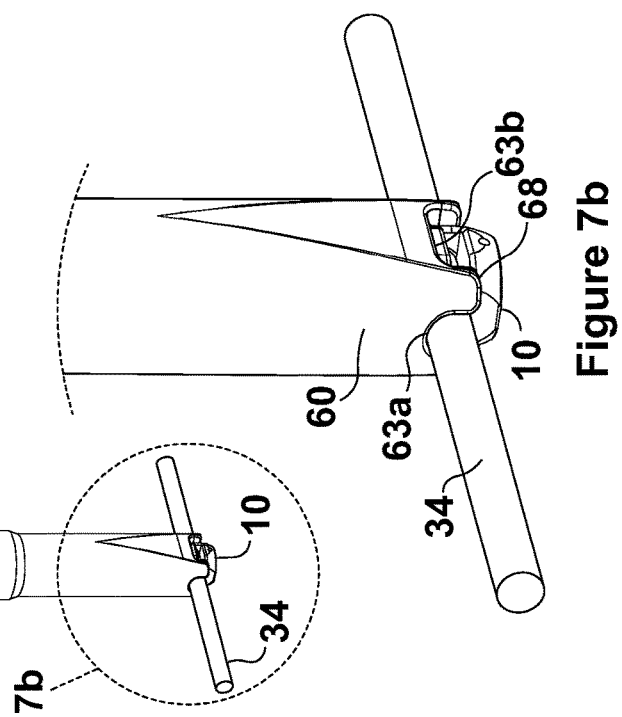
Figure 6a
Figure 6b
Figure 7a
Figure 7b

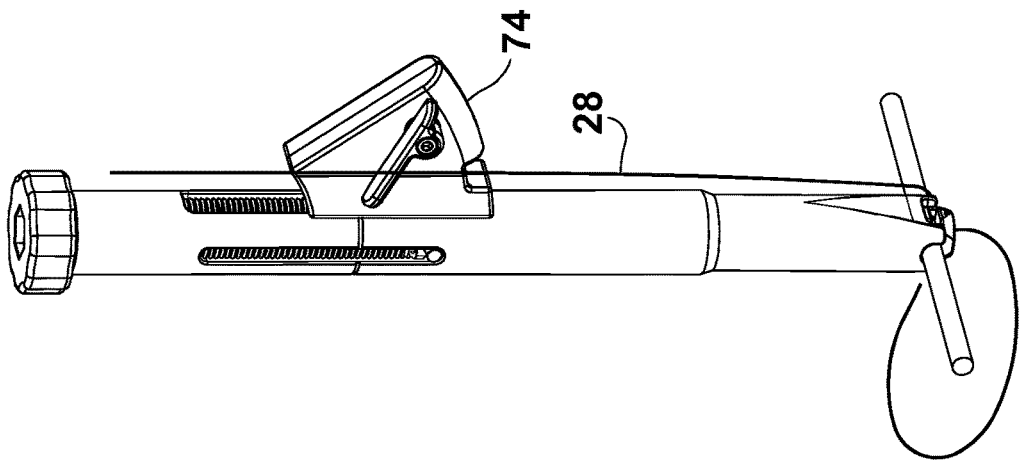
Figure 8
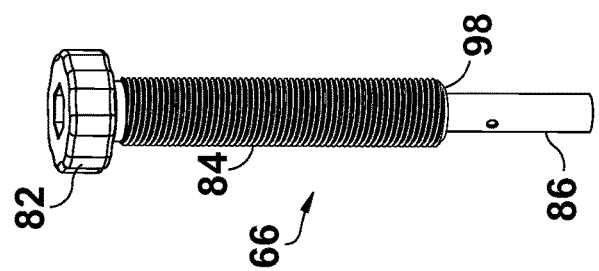
Figure 7g
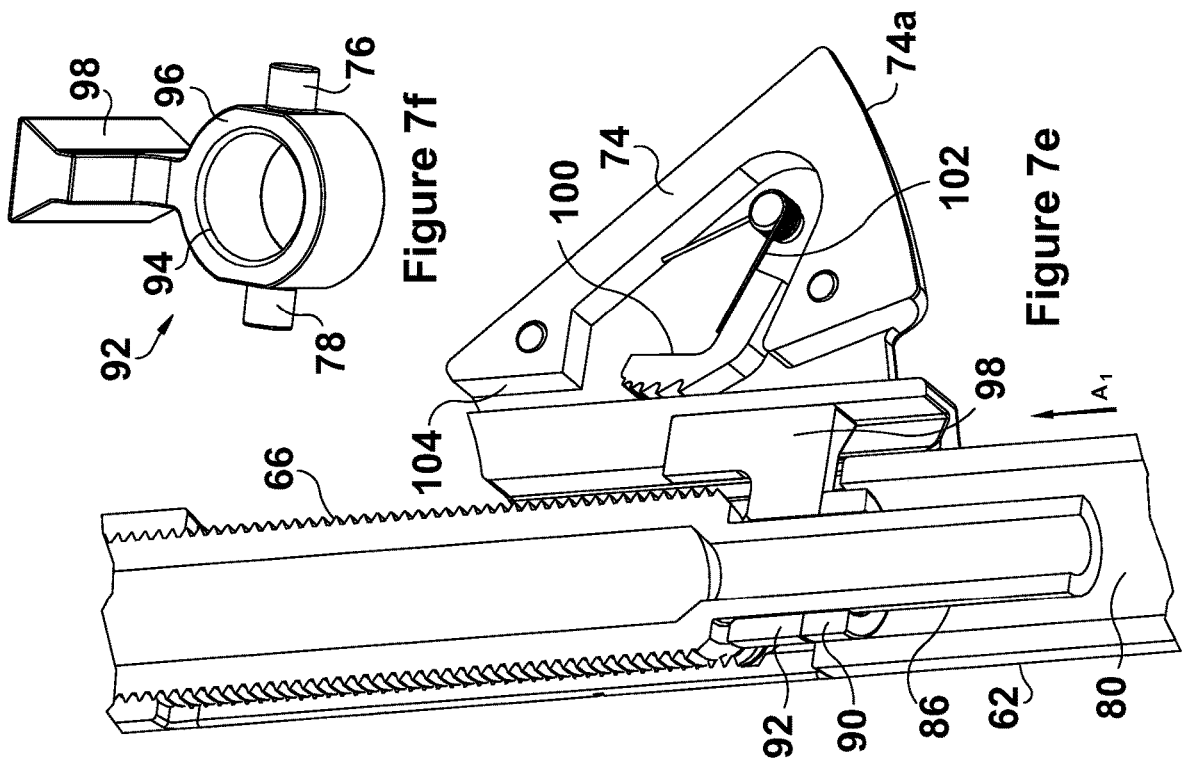
Figure 7f
Figure 7e

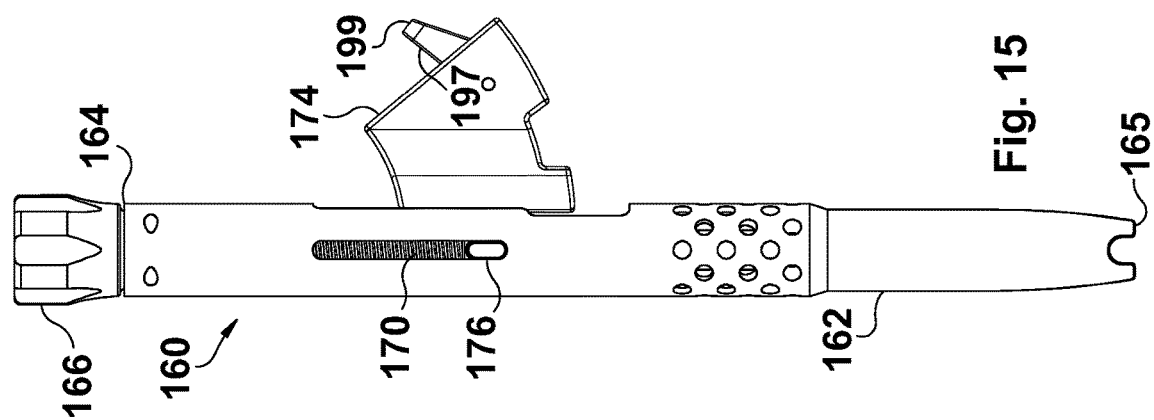
Fig. 15
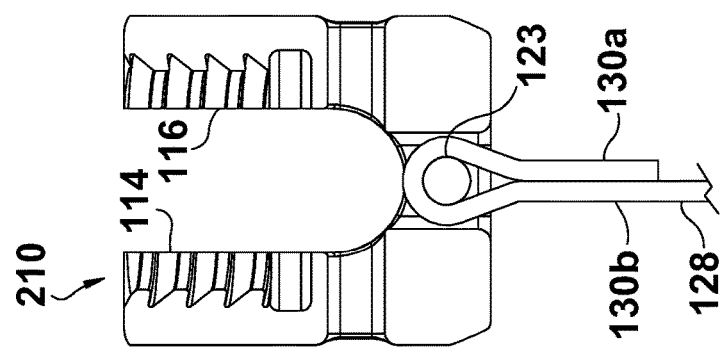
Fig. 14
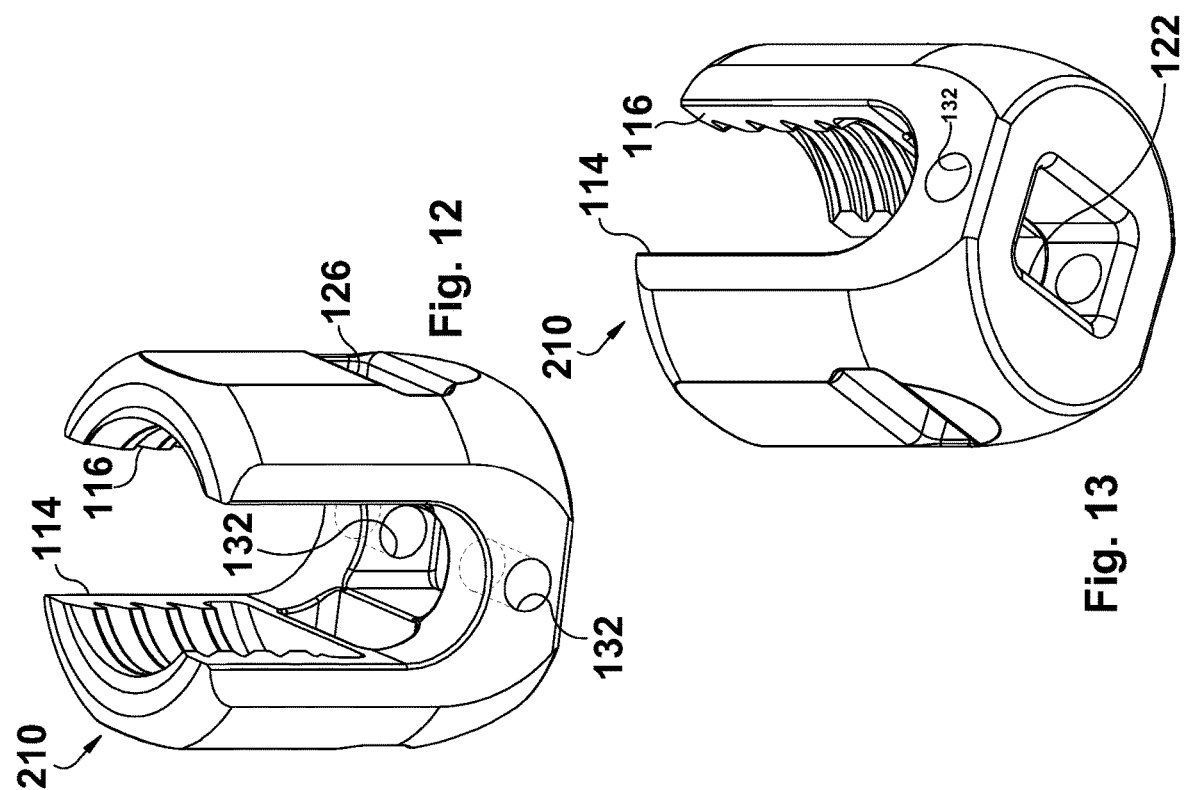
Fig. 12
Fig. 13

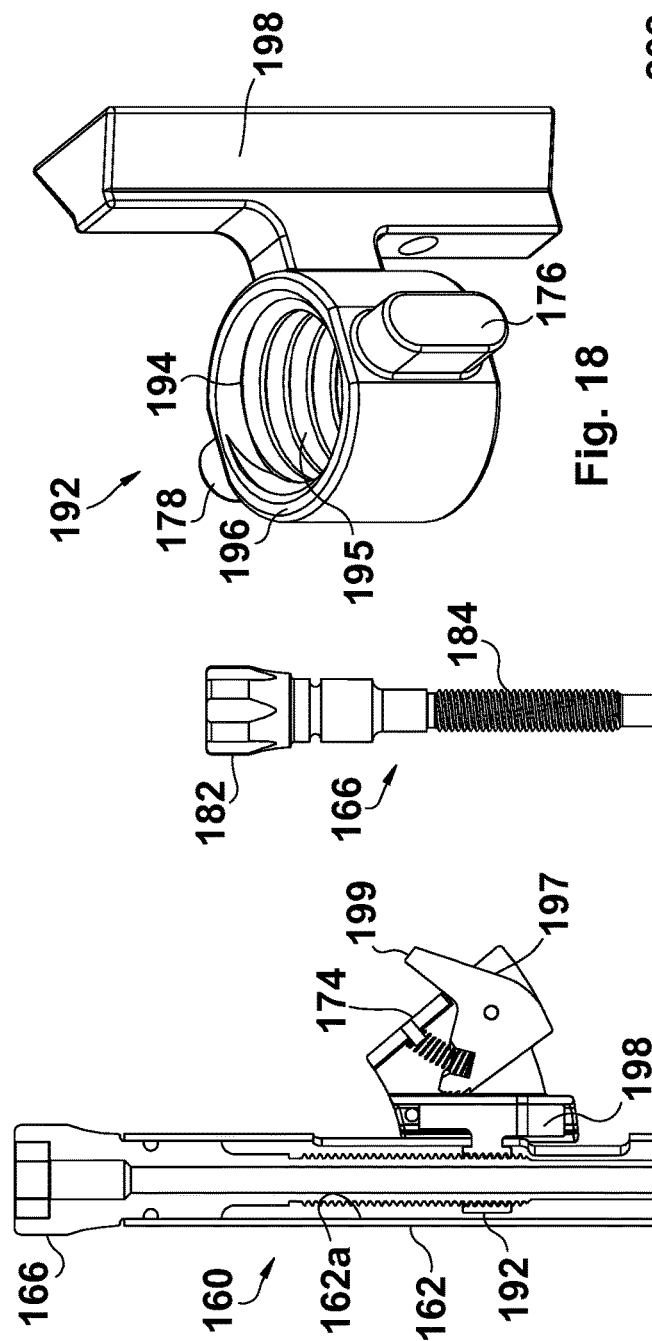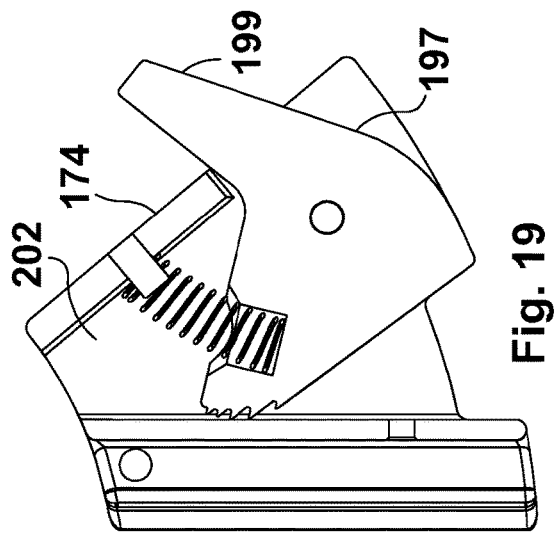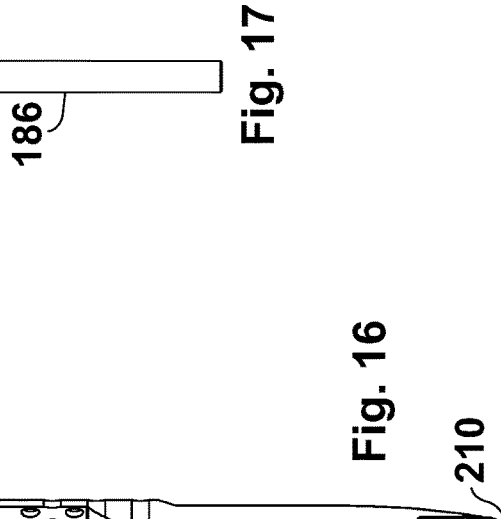

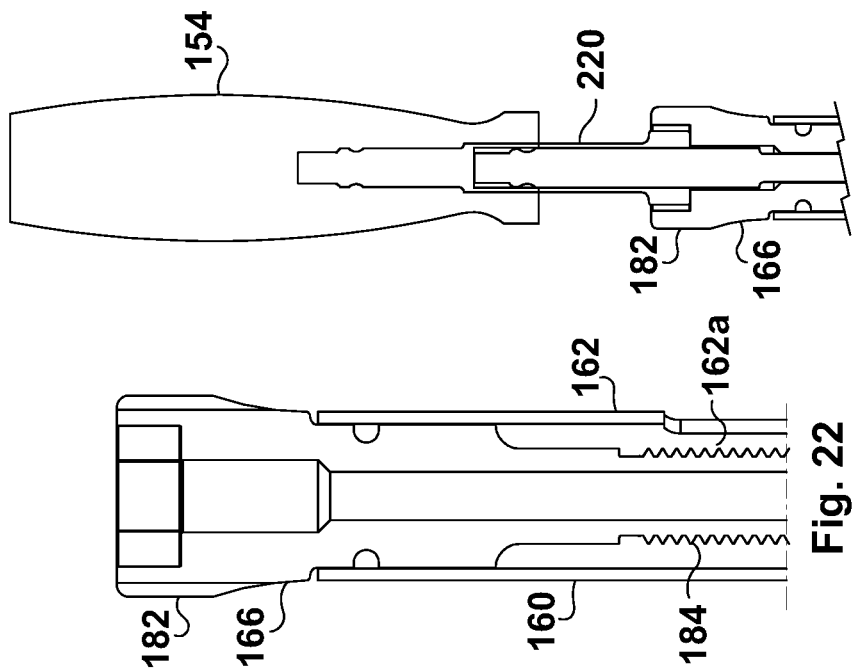
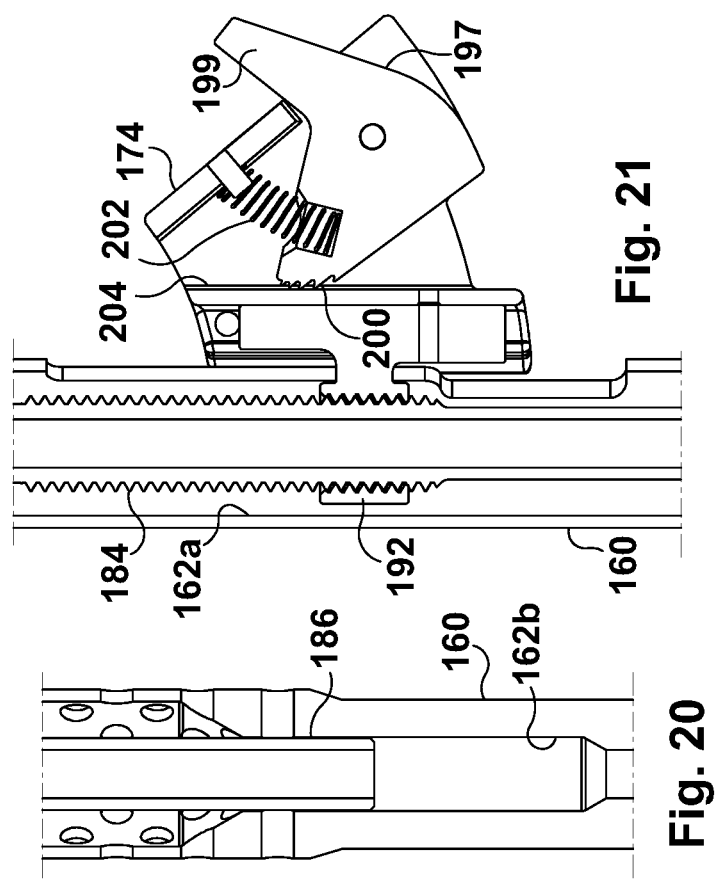

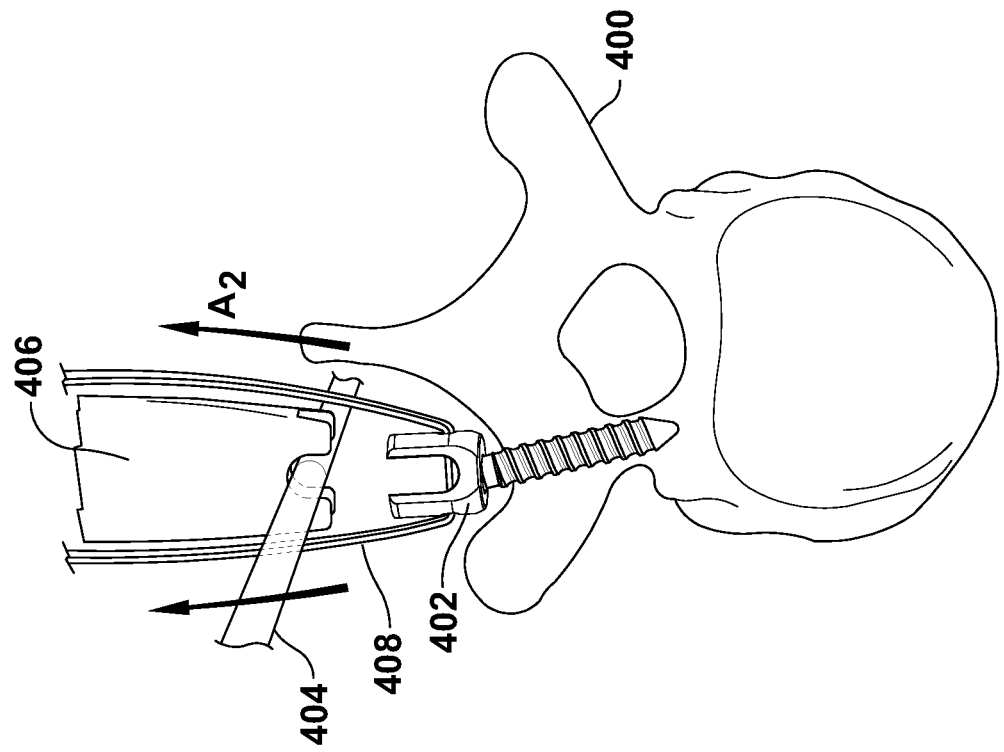
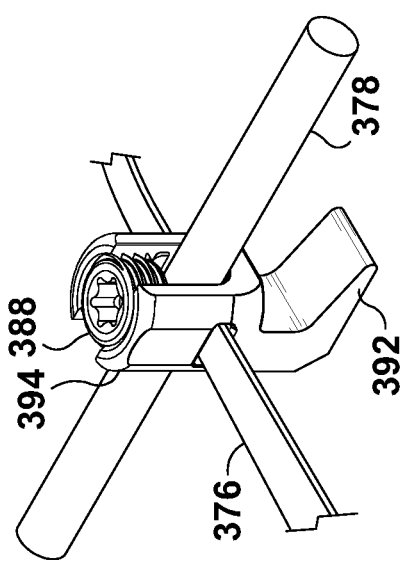
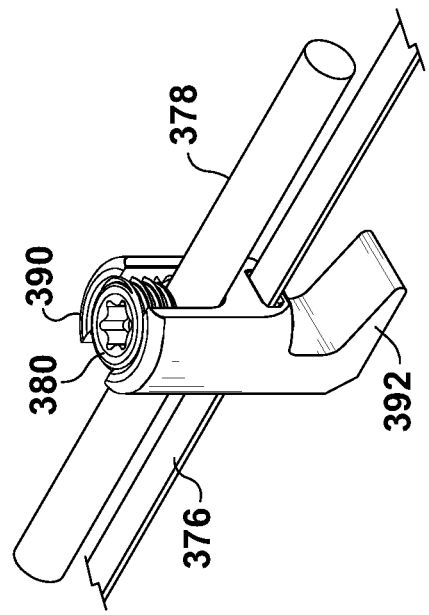

ORTHOPEDIC TETHERED IMPLANTS AND SYSTEM

CROSS-REFERENCE TO RELATED APPLICATION

This application claims the benefit of priority under 35 U.S.C. § 119(e) to U.S. Provisional Patent Application Ser. No. 62/366,866, entitled ORTHOPEDIC TETHERED IMPLANTS AND SYSTEM, filed Jul. 26, 2016, and is a continuation in part of and claims the benefit of priority to U.S. patent application Ser. No. 15/058,582, entitled TETHER CLAMP & IMPLANTATION SYSTEM, filed Mar. 2, 2016, now issued U.S. Pat. No. 9,770,268, and which is also a continuation in part of and claims the benefit of priority to U.S. patent application Ser. No. 14/746,226, entitled TETHER CLAMP & IMPLANTATION SYSTEM, filed Jun. 22, 2015, now issued U.S. Pat. No. 9,770,267 and from which U.S. patent application Ser. No. 15/058,582 claims priority as a divisional application, which is a divisional application of and claims the benefit of priority to U.S. patent application Ser. No. 13/618,724, now issued U.S. Pat. No. 9,173,685, entitled TETHER CLAMP & IMPLANTATION SYSTEM, filed Sep. 14, 2012, which claims the benefit of priority under 35 U.S.C. § 119(e) to U.S. Provisional Patent Application Ser. No. 61/534,453, entitled TETHER CLAMP AND IMPLANTATION SYSTEM, filed Sep. 14, 2011, and which claims the benefit of priority under 35 U.S.C. § 119(e) to U.S. Provisional Patent Application Ser. No. 61/595,296, entitled TETHER CLAMP AND IMPLANTATION SYSTEM and filed Feb. 6, 2012, the entire disclosure of each of which is incorporated herein by reference, to the extent that either is not conflicting with the present application.

BACKGROUND

The human skeleton is formed of bones, each bone performing a structural role, either individually or collectively with other bones. A variety of conditions, including injuries, degeneration, and congenital abnormalities can present the need for interventional procedures to achieve one or more of bone repair, stabilization, and correction. Conventional procedures have been developed using mechanical implants, for example to straighten or otherwise hold fractured bones or successive vertebrae in a fixed position. These include screws and rods, bands, plates, and combinations of these devices which are comprised of metal. Due to the rigidity of these devices, there is a need for systems that provide greater flexibility and adjustability.

For example, the spine is made up of approximately 24 vertebrae, each composed of several portions, which act as a whole to surround and protect the spinal cord and nerves, provide structure to the body and enable fluid body motion in many planes. The vertebrae are normally aligned along an axis, with each vertebra presenting a posterior wall from which projects a spinous process and two side edges having walls from which project the ribs and/or transverse processes. An individual's spine may be damaged or otherwise compromised in one of many ways. A spine may present an abnormal curvature, such as for example, vertebrae inclined and rotated relative to one another and relative to the vertebral axis. In such a curvature, the lateral edges of the vertebrae situated on one side are closer to one another and form a concave curve, while the lateral edges on the other side are spaced apart from one another and form a convex curve. This condition can result in subsequent and serious conditions, such as for example, abnormalities of the cardiac, pulmonary, neuromuscular and gastrointestinal systems.

An individual's spine may also be damaged by one or more fractured vertebrae. Spine osteosynthesis, the reduction (bringing together) and fixation of a bone fracture with implantable devices, is a known treatment of a spinal fracture. Specifically, osteosynthesis is a surgical procedure with an open or percutaneous approach to the fractured bone, which aims to bring the fractured bone ends together and immobilize the fracture site while healing takes place.

To correct these and other conditions, conventional procedures have been developed using mechanical implants to straighten or otherwise hold successive vertebrae in a fixed position. To keep the vertebrae in the desired relative position, hardware, such as a screw, is inserted into the vertebrae. The screws include tulip heads and act as an anchoring point for a connecting member between vertebrae, such as a straight surgical rod.

The use of screws introduces risk into the surgical procedure and may cause additional damage to the vertebrae. Spinal clamps have been developed that provide additional anchor points along the spine when the use of a screw is not possible or not optimal. Known exemplary spinal clamps introduce further risk and complexity into the surgery, including installation complexity, inadequate size offerings and additional parts.

Similar risk and complexity exist in orthopedic surgery in other areas of the body adjacent or remote from the spine.

SUMMARY

The present application describes various exemplary methods and apparatus for tether clamps and tether clamp instruments and systems, together with methods for addressing orthopedic conditions using tether bands and associated implants and instruments.

In various embodiments, a clamp assembly includes a clamp housing, a securement assembly selected from discrete locking and securement elements, and an integrated locking and securement element, and a flexible band or tether. The clamp housing is in some embodiments unitary (one piece), have no moving parts, and defines at least one slot for passage of the band. The housing is adapted to receive the securement assembly, which may comprise a screw, snap or spring element, or a rod or other insert, in some embodiments without the use of a retaining clip or other hardware for retaining the securement assembly in the housing. The securement assembly provides at least the compressive force for retaining and fixing the tether band to the housing. And in some embodiments, the securement assembly is further used for providing securement, alignment, stabilization or other benefits within the clamp assembly.

In various embodiments, the securement assembly is positioned within a recess in the clamp housing to provide compressive force onto the band to compress the band against an interior surface of the housing after tensioning to achieve fixed engagement of the band within the housing. In some embodiments, the housing and the securement assembly engage in each of a provisional and a fixed locking engagement, thereby enabling provisional (temporary) fixation of the band to the clamp in preparation for locking of the securement assembly once desired tether band tension and positioning have been achieved. In some embodiments, the housing defines an axis along the recess, and in some such embodiments, all or a portion of the housing is cylindrical, as well as all or a portion of the recess, and according to such embodiments, all or a portion of the securement assembly is engaged co-axial with one or both of the recess and the housing. During installation, the band is tightened around one or more of a bone and another implant and tensioned into a tightened position by use of a tensioning instrument.

In some particular embodiments, as described herein, the securement assembly is retained within the housing. In yet other particular embodiments, as described herein, the securement element includes a locking set screw and a surgical rod that extends beyond the housing of a clamp assembly for attachment with one or more other implants, such as other clamp assemblies, screws, and plates.

In some embodiments, a clamp system includes a clamp assembly, locking and tensioning tools, and a tensioning instrument, as described in some representative embodiments herein. The tensioning instrument has a distal end which engages the clamp assembly. The tensioning instrument further defines at least one slot which allows movement of a carriage between a non-tightened position and a tightened position, permitting a surgeon to tighten the band. A longitudinal cylinder of the tightening instrument permits the insertion of various tools, e.g., to restrict movement of the vertebral structure relative to the securement assembly. In some embodiments, the base of the clamp assembly may include one or more surface features including elevating feet, knurling or other surface texturing, ribs, and apertures for receiving one or more of hooks, bone screws, nails, plugs or wires to affixing the clamp to bone.

An embodiment of a method includes, by way of example, positioning a clamp assembly adjacent to a bone or portions of a bone (such as across a fracture), and includes: providing a clamp assembly including a clamp housing, a securement assembly comprising a locking element a securement element, and a band, wherein in some particular embodiments the locking element is a set screw and the securement element is a spinal rod. The method further includes positioning the housing along the rod at a desired location adjacent a bone, such as a fractured long bone; wrapping a band about the aligned portions of the fractured bone and through the housing; inserting the locking element within the housing to capture the securement element; provisionally locking the locking element; engaging a tensioning instrument with the clamp assembly; inserting the band through a carriage of the tensioning instrument; moving the carriage to a tightened position to secure the band; locking the locking element, and disengaging the tensioning instrument.

BRIEF DESCRIPTION OF THE RELATED DRAWINGS

Features and advantages of the general inventive concepts will become apparent from the following detailed description made with reference to the accompanying drawings.

Figure A1 depicts positioning of a clamp assembly according to the invention for rib cerclage;

Figure A2 depicts positioning of a clamp assembly according to the invention for fracture securement;

Figure A3 depicts in six views a first embodiment of a clamp assembly according to the invention, including from top left to bottom right, a semitransparent top surface view, a top perspective view, a cross sectional side view, a side view, a semitransparent bottom view, and a bottom perspective view;

Figure A4 depicts in five views a second embodiment of a clamp assembly according to the invention, including from top left to bottom right, a semitransparent top surface view, a top perspective view, a cross sectional side view, a side view, and a semitransparent bottom view;

Figure A5 depicts in five views a third embodiment of a clamp assembly according to the invention, including from top left to bottom right, a semitransparent top surface view, a top perspective view, a cross sectional side view, a side view, and a semitransparent bottom view;

Figure A6 depicts in six views a fourth embodiment of a clamp assembly according to the invention, including from top left to bottom right, a semitransparent top surface view, a top perspective view, a cross sectional side view, a side view, a semitransparent bottom view, and a bottom perspective view;

Figure A7 depicts in six views a fifth embodiment of a clamp assembly according to the invention, including from top left to bottom right, a semitransparent top surface view, a top perspective view, a cross sectional side view, a side view, a semitransparent bottom view, and a bottom perspective view;

Figure A8 depicts in three panels, from left to right of cross sectional side and side views of embodiments of a clamp assembly according to the invention, where Figure A8 A1 is a cross sectional side view showing a first path for a band;

Figure A8 A2 is a side view of the clamp assembly;

Figure A8 B1 is a cross sectional side view showing a first path for a band;

Figure A8 B2 is a side view of the clamp assembly;

Figure A8 C1 is a cross sectional side view showing a first path for a band;

Figure A8 C2 is a side view of the clamp assembly;

Figure A9 shows on the left top and side views of an embodiment of a clamp assembly according to the disclosure, and on the right top and side views of a first embodiment of a securement assembly of the clamp assembly;

Figure A10 shows on the left top and side views of another embodiment of a clamp assembly according to the disclosure, and on the right top and side views of a second embodiment of a securement assembly of the clamp assembly;

FIG. 1a is a front perspective view of a spinal clamp housing;

FIG. 1b is a side perspective view of the housing of FIG. 1a;

FIG. 1c is a front view of a band wrapped about the housing of FIG. 1a;

FIG. 1d is a bottom perspective view of the housing of FIG. 1a;

FIG. 5a is a perspective view of a provisional locking tool engaged with a rod and spinal clamp assembly, shown without a band;

FIG. 5b is an enlarged perspective view of the designated circular area of FIG. 5a;

FIG. 5c is a perspective view of the provisional locking tool of FIG. 5a;

FIG. 6a is a front view of a tensioning instrument;

FIG. 6b is a rear view of the tensioning instrument of FIG. 6a;

FIG. 7a is a front perspective view of the tensioning instrument of FIG. 6a, shown engaged with the rod and spinal clamp assembly of FIG. 5a;

FIG. 7b is an enlarged perspective view of the designated circular area of FIG. 7a;

FIG. 7e is a perspective cross-sectional view of a center portion of the tensioning instrument of FIG. 7a;

FIG. 7f is an enlarged perspective view of a bearing ring of the tensioning instrument of FIG. 7a;

FIG. 7g is a front perspective view of a tightening rod of the tensioning instrument of FIG. 7a;

FIG. 8 is a perspective view of FIG. 7a, shown with the band routed through a carriage of the tensioning instrument, with the carriage in a non-tightened position;

FIG. 9b is a front cross-sectional view of the carriage of FIG. 9a;

FIG. 10b is perspective view of a tightening tool of FIG. 10a;

FIG. 11c is a side view of the screwdriver tool of FIG. 11a;

FIG. 12 is a front perspective view of another spinal clamp housing;

FIG. 13 is a bottom perspective view of the spinal clamp housing of FIG. 12;

FIG. 14 is a front sectional view of the spinal housing of FIG. 13, shown with a pin and band installed in the housing;

FIG. 15 is a front view of a tensioning instrument;

FIG. 16 is a front sectional view of the tensioning instrument of FIG. 15;

FIG. 17 is front view of a tightening rod of the tensioning instrument of FIG. 15;

FIG. 18 is a perspective view of a bearing ring of the tensioning instrument of FIG. 15;

FIG. 19 is a front cross-sectional view of the carriage of FIG. 15;

FIG. 20 is a cross-sectional view of a center portion of the tensioning instrument of FIG. 15;

FIG. 21 is a cross-sectional view of a center portion of the tensioning instrument of FIG. 15, shown with the tightening rod installed and the carriage in a non-tightened position;

FIG. 22 is a cross-sectional view of a top portion of the tensioning instrument of FIG. 15, shown with the tightening rod installed;

FIG. 23 is a cross-sectional view of a top portion of the tensioning instrument of FIG. 15, shown with the screwdriver tool installed;

FIG. 31a is a perspective view of another embodiment of the invention, showing a tether band/rod/hook assembly;

FIG. 31b is a perspective view of another embodiment of the invention, showing another tether band/rod/hook assembly; and FIG. 32 is a front view of a tether band/pedicle screw assembly as used in a reduction process.

Figure 3:
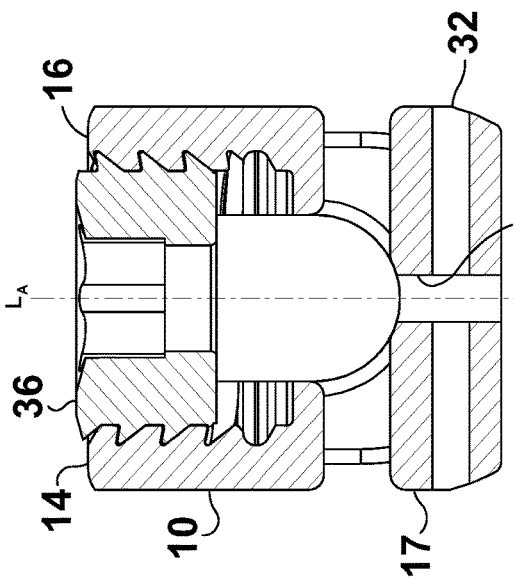
FIG. 3 is a front cross-sectional view of a set screw positioned within the housing of FIG. 1a, shown without a rod or band.

Implants and instruments in accordance with these applications can include the features as described further herein in connection with the following disclosure:

DETAILED DESCRIPTION

This Detailed Description merely describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The invention is directed to a tether clamp assembly and implantation system for use in orthopedic surgery. The system provides a temporary or permanent implant intended to provide temporary stabilization during the development of solid bony fusion and aid in the repair of bone fractures. Exemplary indications for use include, but are not limited to: spine to rib fixation; cerclage banding for fractures and osteotomies, and, anterior spinal tethering, as well as spinal fixation applications, such as spinal trauma surgery, used in sub-laminar, interspinous, or facet wiring techniques, spinal reconstructive surgery, incorporated into constructs for the purpose of correction of spinal deformities such as scoliosis, kyphosis, spondylolisthesis, spinal degenerative surgery, as an adjunct to spinal fusions, and treatment of idiopathic and neuromuscular scoliosis in patients eight years of age and older.

The inventive system may be used in conjunction with other medical implants made of metal, for example, titanium alloy or cobalt chromium alloy, whenever "wiring" or banding may help secure the attachment of other implants. Of course it will be appreciated that while many of the specific exemplary embodiments shown in this supplemental disclosure are directed to spinal applications, the invention herein is capable of application to any orthopedic subject matter in humans and animals, and there is no limitation as to the use hereof with other anatomical structures, such as long bones, ribs, major joints such as the shoulder, hip and knees, and aspects of the spine, to name a few.

An embodiment of the invention which will now be discussed is an orthopedic clamp implant. Referring now to the drawings, Figures A1 and A 2 show representative examples of use of an orthopedic implant comprising a clamp assembly according to the disclosure, wherein Figure A1 shows an assembly in the context of use for rib cerclage, and Figure A2 shows an assembly in the context of use for bone fracture securement. With reference generally to Figures A1-A10, in accordance with the various embodiments, a clamp assembly 500 includes a clamp housing 510, a securement assembly 600, and a flexible band 700.

Referring again to the drawings, Figures A3-A7 show alternate embodiments of a clamp housing 510 according to the disclosure. The housing is adapted for placement at a desired implantation point in contact with or generally adjacent to bone, such as but not limited to one or more of a vertebra, a long bone, and a rib. The clamp housing 510 may be constructed of suitable material, such as for example, stainless steel, cobalt chromium, or titanium.

The housing includes a base 540 that may be generally cylindrical shaped, or plate like and one of round or square. The clamp housing includes a top surface 550 that includes an opening 555 into a recess 560, and a bottom surface 590. In some embodiments, as shown, the top surface 550 is generally cylindrical with a circular opening 555. The recess 560 defines a longitudinal axis $L_A$ and the recess 560 extends from the top surface 550 towards the base 540. The clamp housing 510 also includes a bottom surface 520 and a side surfaces 530. In some embodiments, as depicted in FIGS. 1A-10A, the base 540 is generally square shaped and the side surfaces 530 form four discrete sides. An internal surface of the recess includes a mating engagement surface 570 comprising a locking feature 580, such as for example, a threaded surface. According to embodiments wherein the locking feature is adapted to engage with a threaded screw or set screw, the threaded surface mates with a locking element 620 component of a securement assembly 600, such as for example, a set screw. In some other embodiments, a locking element 620 is selected from other securement means, such as but not limited to, a blocking nut, or a blocker, and is engageable by snap or other fitting with one or more locking features 580 selected from flanges, grooves, ridges, teeth or the like on the mating surface 570 of the recess 560. It should be apparent to one with skill in the art that other styles, types, and sizes of surfaces for locking elements and tensioning instrument mating can be used in the practice of this invention.

Figure 1E:
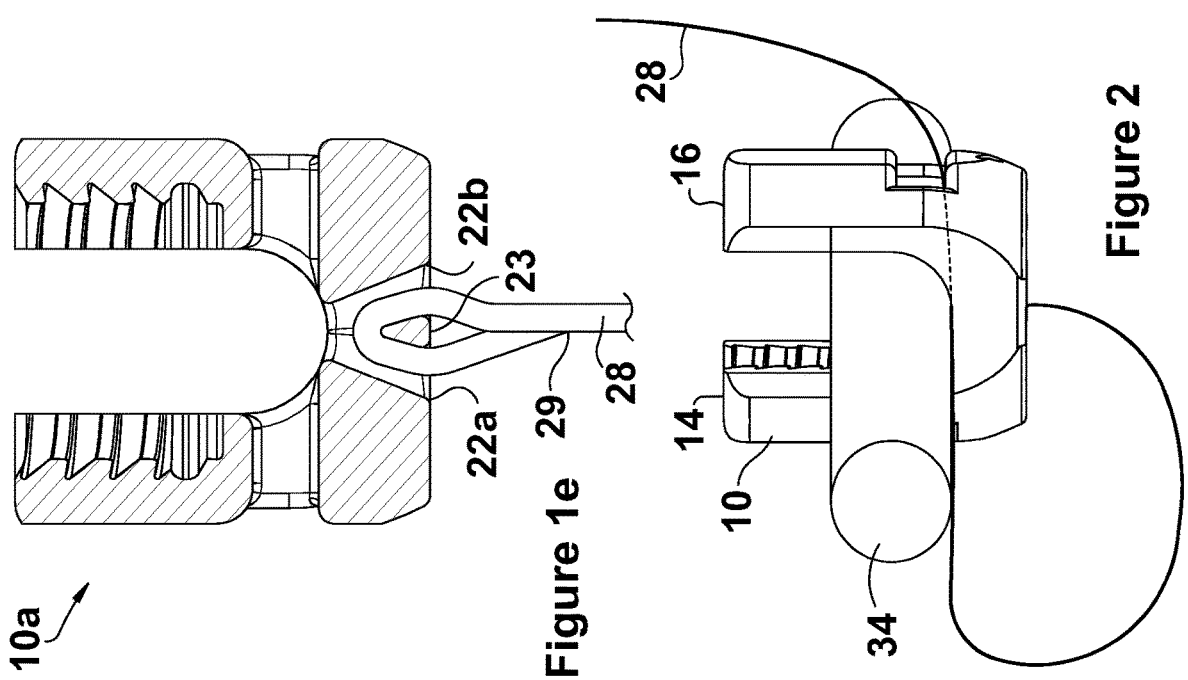
FIG. 1e is a front cross-sectional view of a band engaged with the housing of FIG. 1d.

Generally, the clamp housing 510 according to the various embodiments as disclosed herein includes structural features comprising one or more through slots 590 to permit a band to be wrapped securely about a bone or other structure or another implant, and secured to the housing by passage through one or more through slots. In certain embodiments, the band may be secured at one end by attachment through one or more through slots of the housing (shown, for example, in one possible clamp housing embodiment as depicted in FIG. 1e). For example, one or more of a knot, stitching, and other form of bonding or fixation may formed at one end of the band to secure it to the housing. It should be understood by those with ordinary skill in the art that the number of slots used to secure the band, if any, as well as the shape and location of the slots, may vary in the practice of this invention. It will also be appreciated that in the various embodiments a slot is not limited to an elongate slit that is narrower in a width dimension than in a length dimension, and that a slot may be round, elliptical, or some other shape. Moreover, a band that is fixed at one end to a through slot may partially or completely fill the slot and the slot may compress and end of the band as a means of securement thereto.

The housing 10 further includes apertures 32. These apertures may be used by a surgeon for various purposes, such as for example, grasping the housing 10 during implantation, or insertion of a pin for a structural anchor for another assembly piece, such as for example, the tether band.

Structural features of the bottom of the spinal clamp housing are best seen in Figures A3-A7, wherein it is shown at the bottom surface 520. And various possible band paths defined by the through slots 590 are shown in Figure A8, panels A1, B1 and C1, which show, respectively, passage of the band 700 through each of two bottom and two side slots 590 and passing across the bottom surface 520 of the clamp housing 510, passage of the band 700 through each of two bottom surface 520 slots 590 and passing across an interior surface within the base 540 below the recess 560, and passage of the band 700 through one of two bottom and two side slots 590 and passing over an interior surface within the base 540 below the recess 560 by looping around a side surface 530 of the clamp housing 510.

Referring again to Figures A9 and A 10, each shows alternate embodiments of securement assemblies according to the disclosure, wherein the securement assemblies comprise two parts, including a locking element and a securement element. It will be appreciated that in alternate embodiments, the securement assembly may be unitary and comprise a single component that includes features for engagement within the recess and also contacting the band 700 to enable engagement and fixation of band tensioning. As shown in Figure A9, the locking element 620 is a set screw and the securement element 610 is a plug that snap fits into the locking element 620. Referring now to Figure A10, the alternate embodiment of a securement assembly 600 includes a locking element 620 comprising a blocker or blocking nut that engages with one or more locking features 580 in the recess 560, and a securement element 610 similar to that of Figure A9. In accordance with the various embodiments, the securement element 610 may be provisionally engaged with the band 700 by actuation through an opening in the set screw and upon final tensioning of the band 700, the set screw and plug are actuated to fully engage with and lock within the housing to secure the band to the housing and secure the tightened band for therapeutic use.

Generally, in some embodiments the securement assembly may include other fastener and engagement features, such as but not limited to a dowel pressed through set screw and into groove on a plug for actuation of the plug into engagement with the band, and it may include a flexible retaining ring assembled into a locking element such as a set screw that snaps into a groove on the plug. In yet other embodiments, the plug may have flexible or slotted ends that allow it to snap into the set screw. These alternate embodiments are but some of the ways by which the securement assembly components including locking and securement elements may be fixed to one another.

According to various embodiments of methods as disclosed herein, the instruments described herein below may be adapted for use with one or more of the clamp assemblies described herein above and shown in the Figures A1-A10. As used, the instruments may engage the clamp housing 510 to secure it in place while tensioning the band that is fixed at one end to the clamp housing 510 via passage through one or more slots 590, and the various instruments can be used to insert and provisionally secure and finally lock the securement assembly upon final tensioning of the band.

Another embodiment of the invention which will now be discussed is a spinal clamp implant. The spinal implant is used to aid in fusion and stabilization in one or more vertebrae during a posterior access surgery. The spinal clamp can be used with one or more similar spinal clamps to provide anchoring points for a surgical rod. The spinal clamp can further be used with conventional screw and tulip head implants. For example, the spinal clamp may be secured to the third lumbar vertebra L3, while conventional screw and tulip head implants are secured to the second lumbar vertebra L2 and the fourth lumbar vertebra L4. When discussing the spinal clamp and implantation of the spinal clamp, the terms "proximal" and "distal" are used relative to the surgeon, and not the operating field, i.e., not relative the patient.

Referring again to the drawings, a spinal clamp housing 10 is shown in FIGS. 1a and 1b. The housing is adapted for placement at a desired implantation point adjacent to a vertebra. The housing 10 may be constructed of suitable material, such as for example, stainless steel, cobalt chromium, or titanium.

The housing is generally cylindrical shaped and defines a longitudinal axis $L_A$ (best seen in FIG. 3). More specifically, the housing includes a center recess 12 defined by opposing arms 14, 16 extending from a base 17. An internal surface of the arms 14, 16 include a mating engagement surface, such as for example, a threaded surface 18. The threaded surface 18 mates with a locking element, such as for example, a set screw, a blocking nut, or a blocker. An exterior of the exemplary arms 14, 16 include a flat surface 20. A tightening instrument engages the flat surface 20 to prevent housing 10 rotation while the set screw is rotated into a locked position. This operation will be discussed in further detail. It should be apparent to one with skill in the art that other styles, types, and sizes of surfaces for locking elements and tensioning instrument mating can be used in the practice of this invention.

The housing 10 includes structural features to permit a band to be wrapped securely about the housing. A first slot 22 is located at the bottom of the recess 12 and defines a passage for a band along a longitudinal axis of the housing. The first slot may allow use by a surgeon as a starting point for band travel within and in the vicinity of the housing 10. For example, a knot may be tied at the beginning of the band to prohibit one end of the band from entering the slot and passing through to the bottom side of the housing, or one end of the band may include a clip larger in size than the first slot 22. A second slot 24 and a third slot 26 are formed in opposing positions on either side of the housing 10. These slots 24, 26 may permit band travel perpendicular to the longitudinal axis of the housing 10. An exemplary travel path of a band 28 is illustrated in FIG. 1c. The band 28 is illustrated in an exemplary pattern, for example, routed in a pattern around a lamina (not shown).

The housing 10 further includes apertures 32. These apertures may be used by a surgeon for various purposes, such as for example, grasping the housing 10 during implantation, or insertion of a pin for a structural anchor for another assembly piece, such as for example, the tether band.

Structural features of the bottom of the spinal clamp housing are best seen in FIG. 1d. In this embodiment, the housing 10a includes two slots 22a, 22b, separated by a bridge 23, at the bottom of the housing recess. The slots 22a, 22b may allow use by a surgeon as a starting point for band travel within and in the vicinity of the housing 10a. For example, a first end of the band 28 may be routed through both slots as shown in FIG. 1e, and secured to a distal location 29 of the band, to secure the band to the housing 10a. In the exemplary embodiment, the band is integral to the housing and secured prior to surgery, for example, during surgery preparation or by a manufacturer. In other embodiments, the surgeon may attach the first end of the band at the distal location 29 by one of several methods, including sewing the first end to the band. It should be understood by those with ordinary skill in the art that the number of slots used to secure the band, if any, as well as the shape and location of the slots, may vary in the practice of this invention.

Another embodiment of the invention includes a housing having different structural features. Specifically, the housing 210 illustrated in FIGS. 12-14 includes a single aperture 122 at the bottom of housing. The aperture as shown is a rectangular shaped slot. It may be of any suitable shape, width and length. As shown, the single aperature 122 is wider than the double slots 22a, 22b shown in the housing 10 of FIG. 1d.

The base of the housing 210 is absent any apertures oriented perpendicular to a position of an installed surgical rod. The housing 210 does include two holes 132 for supporting a pin 123 as seen in FIG. 14. The holes are positioned co-axial with an installed position of a surgical rod. The end of the band is fixed to provide a loop for slipping over the pin, or the band may be fixed to the pin. As shown, a loop and the end of a tether band 128 is formed by fixing two band lengths 130a, 130b.

Figure 2:
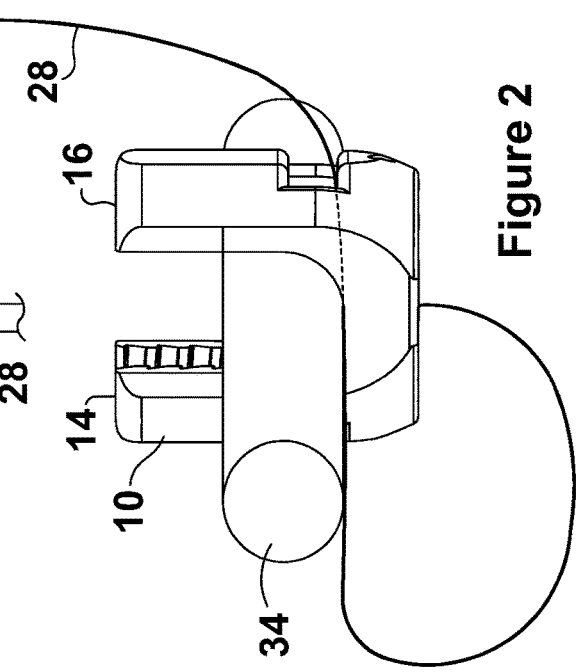
FIG. 2 is a front perspective view of a spinal rod positioned within the housing and band assembly of FIG. 1c.
Figure 7D:
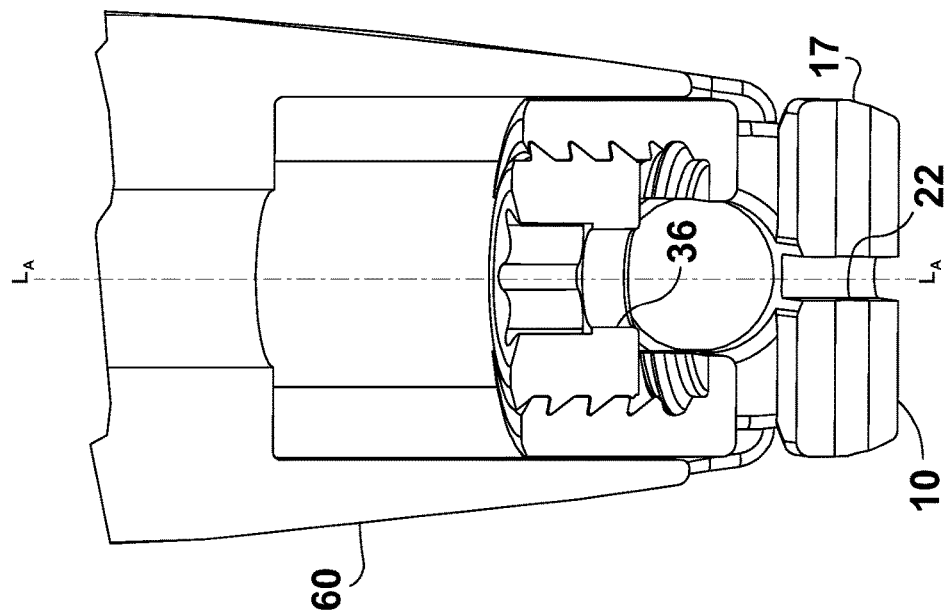
FIG. 7d is an enlarged perspective view of the designated circular area of FIG. 7c.
Figure 7C:
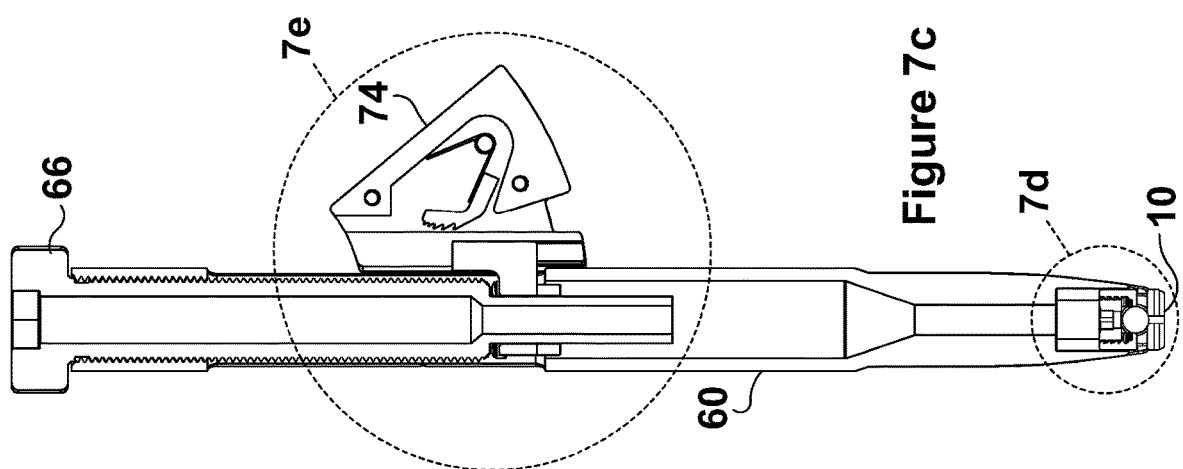
FIG. 7c is a front cross-sectional view of FIG. 7a, shown without a tightening rod.

Referring now to FIG. 2, a surgical rod 34 placed within the recess 12 of the housing is shown. The housing is concave-shaped to accept and laterally retain the rod 34 within the arms 14, 16. The weight of the rod 34 applies a force to pinch a portion of the band 28 against the housing 10. It will be appreciated that in alternate embodiments, a different securement element other than a rod may be used to secure the band within the housing. In some specific embodiments, the fixation element need not extend outside of the housing, and in some embodiments, the housing does not include opposing arms and may be overall cylindrical.

Figure 4:
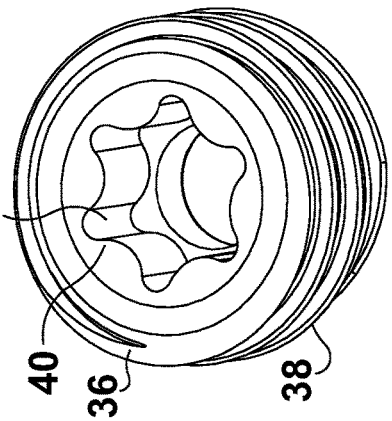
FIG. 4 is a top perspective view of a locking element of FIG. 3.

During implantation, the next step is to provisionally lock the rod in place with use of a set screw. A set screw 36 is shown engaged with a housing 10 in FIG. 3. The rod 34 and band 28 are not shown for clarity. As shown in FIGS. 3 and 4, the set screw 36 has a threaded external circumferential surface 38 which engages the internal threaded surface 18 of the arms 14, 16. A top surface 40 of the set screw 36 includes a cut-out recess 42. The recess 42 is shaped to accept locking tools.

FIGS. 5a and 5b illustrate a provisional locking tool 50 engaged with a set screw 36. In the implantation of the spinal clamp, a surgeon uses the provisional locking tool 50 to tighten the set screw enough to temporarily contain the rod 34. The set screw must not be locked in place until the band is sufficiently tightened about the target lamina. In a further surgical step, the set screw 36 is locked in a final position.

As shown in FIG. 5c, the provisional locking tool 50 includes an instrument rod 52 and palm handle 54. The palm handle 54 may be separable from the instrument rod 52. The system may include multiple tools, each with specifically shaped instrument rods. For example, the instrument rod 52 includes a constant diameter shaft terminating in a socket head 56 sized to mate with the recess 42 of the set screw 36.

The spinal clamp installation system includes a tensioning instrument for use by a surgeon to tighten a band and securing the vertebral structure relative to the implant rod. The installation system is arranged for user ease of installation. As shown in the Figures, for example, FIGS. 3 and 7d, the housing 10, set screw 36 and tensioning instrument 60 are all positionable about a common longitudinal axis $L_A$. Any tools used in the installation, either prior to the engagement of the tensioning instrument, or inserted within the internal channel of the tensioning instrument from a proximal end to a distal end, are also positioned along the same common axis. This arrangement also promotes increased user flexibility, e.g., the user may easily incrementally tighten a band of a spinal clamp assembly, then by retracting a tool from the set screw and then disengaging the tensioning instrument from the housing, move to the next sequential spinal clamp assembly along the surgical rod, and make a similar incremental adjustment.

FIGS. 6a and 6b illustrate front and rear views of a tensioning instrument 60. The instrument includes an elongated cylinder 62. The cylinder permits the insertion of tools from a proximal end 64 to a distal end 65 to manipulate the set screw 36, and further contains a hollow tightening rod 66. The tightening rod 66 is used by the surgeon to secure the band 28 in a final position.

The cylinder 62 is adapted for securing the spinal clamp in a final position relative the target vertebra. FIGS. 7a-7d illustrate various views of the tensioning instrument 60 engaged with a spinal rod. The cylinder 62 includes projections 68 at the distal end 65. An arched section 63a between two adjacent projections engage a top surface of the rod 34 (see FIG. 7b). A flat portion 63b between other adjacent projections engage the flat portions 20 on the exterior of the housing 10, to prohibit movement of the housing. The cylinder further defines two opposing slots 70, 72. The slots permit travel of a carriage 74 within the slot, at least partially between a distal end 70a (see FIG. 7a) and proximal end 70b (see FIG. 10a). Two protruding tabs 76, 78 ride within the slots during movement of the carriage. The mechanics of this movement will be discussed in further detail.

The tensioning instrument is structured to tighten the band 28 to secure the housing 10 to the rod 34. As best seen in FIG. 7e, the cylinder 62 includes an interior surface 80 defining a hollow chamber. Within the proximal portion of the chamber, the tightening rod 66 mates with internal threads of the cylinder. The tightening rod 66 is illustrated in FIG. 7g and includes a knob 82, threaded portion 84, and a distal, non-threaded portion 86. The distal portion 86 includes holes 88 for engagement by set screws (not shown) which secure a retaining ring 90 (see FIG. 7e). The retaining ring 90 moves axially within the cylinder as the tightening rod 66 is manipulated by the surgeon.

A bearing ring 92 is disposed to the proximal side of the retaining ring 90, as best shown in FIG. 7e. Further as shown in FIG. 7f, the two tabs 76, 78 radially protrude from opposing sides of the bearing ring 92. A center aperture 94 permits passing of the distal portion 86 of the tightening rod 66. A top surface 96 of the bearing ring 92 may engage a shoulder 98 of the tightening rod to limit entry of the rod into the cylinder in a distal direction.

The bearing ring 92 is adapted for connection to the carriage 74. As shown in FIG. 7e, a shoulder 98 extends radially from a base of the bearing ring into the carriage 74, which is constructed from two pieces 74a, 74b (see FIG. 9a). The carriage may be constructed of a suitable material, such as for example, plastic or metal, and include two snap-fit pieces that enclose the shoulder 98. A carriage half 74a is illustrated in FIG. 7e and includes a spur 100 which is biased in a direction toward the cylinder 62 by a torsion spring 102. The spur 100 is operated by a handle 103 (see FIG. 9a) to permit threading of the band 28 in a proximal direction through a channel 104 in the carriage 74. Teeth on the spur 100 prohibit return movement of the band in the distal direction.

Figure 9A:
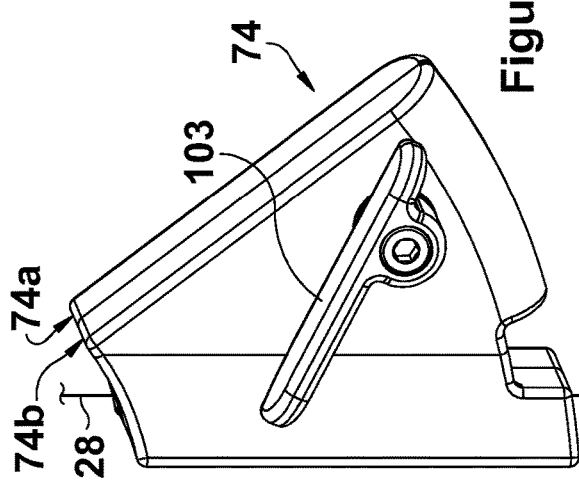
FIG. 9a is an enlarged perspective view of the carriage of FIG. 8.
Figure 9B:
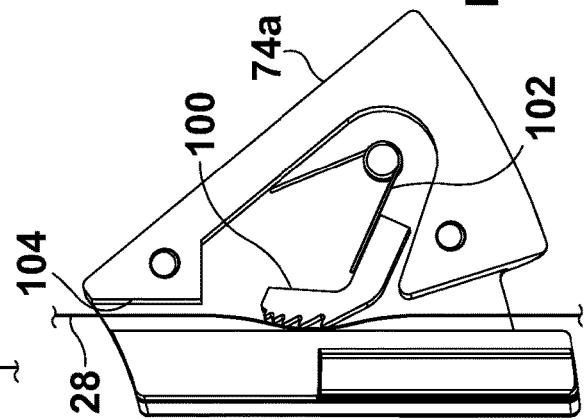

FIG. 8 shows the band 28 inserted through the carriage 74 and properly positioned for use of the tensioning instrument. The carriage is in a non-tightened position in FIG. 8. Front perspective and cross-sectional views of the carriage 74 are shown in FIGS. 9a and 9b, respectively, with the band 28 in an inserted position. As shown in FIG. 9b, teeth on the spur 100 press the band 28 against the wall of the channel 104.

Figure 10A:
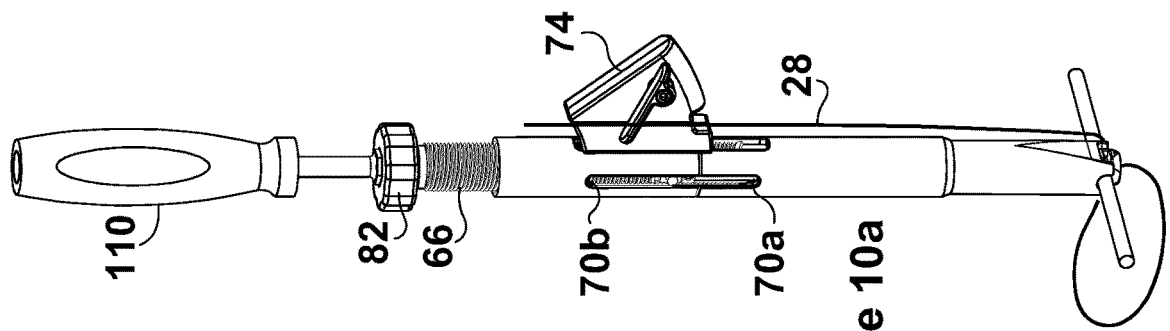
FIG. 10a is a perspective view of FIG. 8, shown with the carriage in a tightened position.

As previously discussed, a surgeon may secure the housing 10 in place relative to the targeted vertebra by manipulation of the tightening rod 66. Referring now to FIG. 10a, a tightening tool 110 is shown engaged with the knob 82 of the tightening rod 66. As shown, the rod 66 has been turned and axially moved in a proximal direction away from the housing 10. As such, the carriage has moved axially along the exterior of the cylinder 62, and within the range between the slot 70 distal end 70a and proximal end 70b, at the discretion of the surgeon. As the carriage moves proximally, the band 28 is tensioned in a proximal direction securing the vertebral structure relative to the implant rod. The carriage is in a tightened position in FIG. 10a.

Figure 10B:
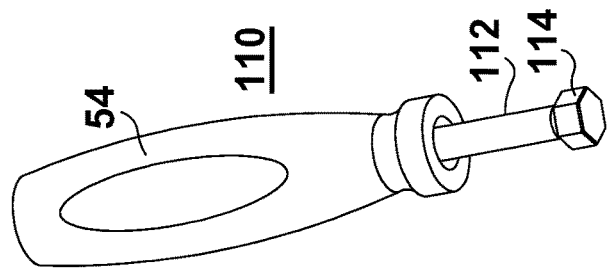

FIG. 10b is a perspective view of the tightening tool 110 of FIG. 10a. The tightening tool includes a palm handle 54 and an instrument shaft 112, which terminates at a head 114 for engaging a recess in the knob 82. As previously discussed in regard to other tools, the palm handle 54 may separate from the instrument shaft 112 so that a single handle can accommodate multiple shafts for multiple purposes during implantation.

Figure 11C:
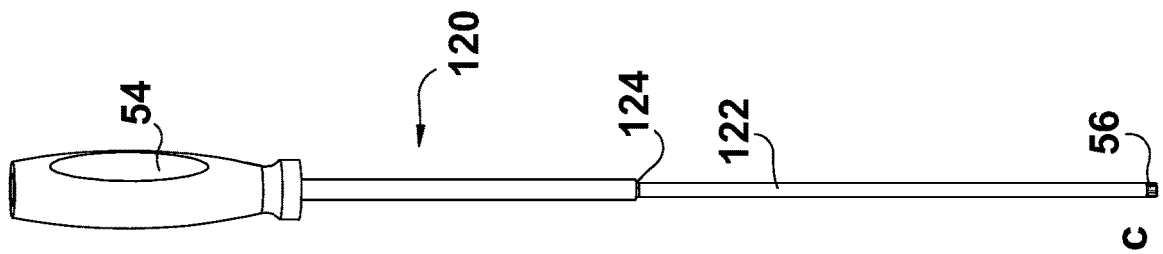
Figure 11B:
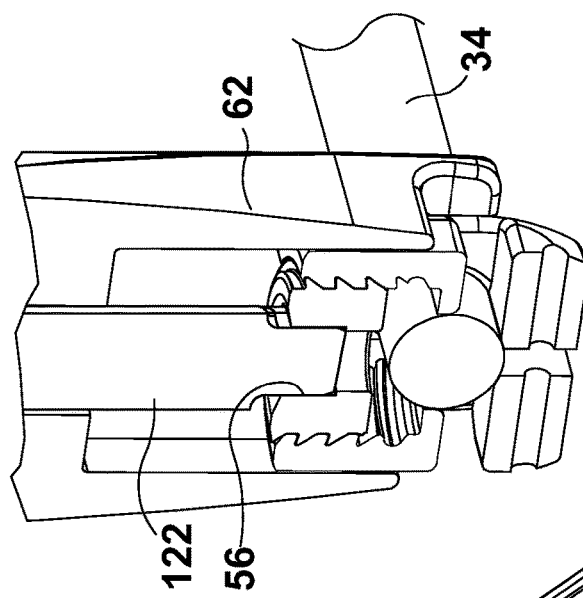
FIG. 11b is an enlarged cross-sectional view of the screwdriver tool engaging the set screw.
Figure 11A:
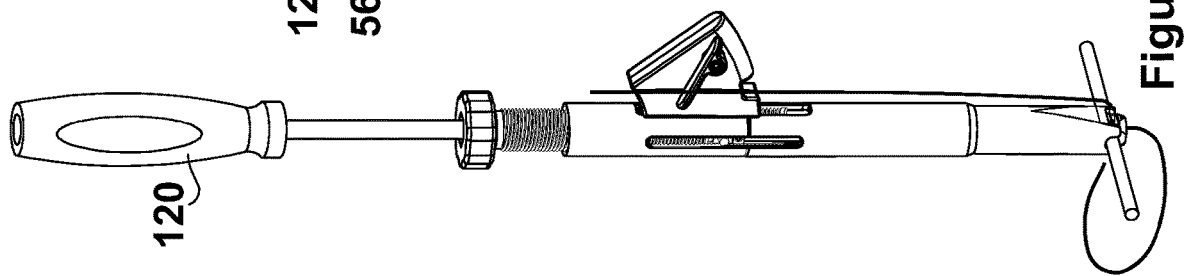
FIG. 11a is a perspective view of FIG. 10a, shown with the carriage in a tightened position and a screwdriver tool inserted within the tensioning instrument.

After the band 28 is sufficiently tensioned, the surgeon may lock the set screw 36 into a desired and final position. FIGS. 11a-11c detail aspects of this locking process. In FIG.

11a, a perspective view of FIG. 10a is shown with the carriage in a tightened position, the tightening tool 110 removed, and a screwdriver tool 120 inserted within the tensioning instrument 60. An enlarged cross-sectional view of the head 56 of the screwdriver tool 120 engaged with the set screw 36 is shown in FIG. 11b. In this position, the surgeon may tighten the set screw as desired by turning the screwdriver tool 120.

FIG. 11c is perspective view of the screwdriver tool 120. The tool includes a palm handle 54 and an instrument shaft 122, which terminates at a head 56 for engaging the recess 42 in the set screw. As previously discussed in regard to other tools, the palm handle may separate from the instrument shaft. The exemplary shaft 122 shown includes a shoulder 124 to accommodate the internal dimensions of the cylinder 62 and tightening rod 66.

Another embodiment on the tensioning instrument will now be discussed. The tensioning instrument 160 and related parts are illustrated in FIGS. 15-23. The tensioning instrument 160 has similar features as the discussed embodiment of FIGS. 5a-11b. However, the tensioning instrument 160 includes structural differences of certain components related to tensioning. The embodiment discussed is exemplary only, and other structural difference of the same or different components can be utilized in the practice of the invention.

FIGS. 15 and 16 illustrate front and sectional views, respectively, of a tensioning instrument. The tensioning rod 166 is fixed by one or more pins and moves only axially upon rotation. In other words, the tensioning rod does not translate along the longitudinal axis of the tensioning instrument. As seen in FIGS. 16, 17 and 18, the inside of the bearing ring is threaded, and no retaining ring or set screws are included in the assembly as in other embodiments. The cross-sectional view of FIG. 21 shows detail of the tensioning rod, bearing ring and carriage assembly.

Referring specifically now to FIG. 15, a front view of a tensioning instrument 160 is illustrated. The tensioning instrument includes a hollow cylinder 162. As best shown in the sectional view of FIG. 16, the cylinder has a smooth internal surface 162 without female threads. With the internal surface being smooth, the threaded portion 184 of the tightening rod 166 does not engage the inside surface of the hollow cylinder 162. As shown in FIGS. 16-18 and 21, the tightening rod 166 engages a bearing ring 192. Specifically, a threaded surface 184 of the tightening rod engages an inside threaded surface 195 of the bearing ring 192.

The bearing ring 192 is adapted for connection to the carriage 174. As shown in FIG. 18, a wing 198 extends radially from a base of the bearing ring. The wing extends into the carriage 174 as in a previously discussed embodiment. Two tabs 176, 178 are oval in shape and ride with a slot 170 on either side of the tensioning instrument 160 as the carriage travels from a lower non-tensioned position to a higher tensioned position, as previously discussed.

The carriage advantageously "auto-locks" in operation, prohibiting disengagement of the band in the distal direction, but allowing for easy slack removal by pulling in the proximal direction.

The carriage 174 illustrated in FIGS. 16 and 19 includes a lever 200 which is biased in a direction toward the cylinder 162 by a torsion spring 202. The lever 200 is operated by a handle 199 to permit threading of a tether band in a proximal direction through a channel 204 in the carriage 174. Teeth 197 on the lever 200 prohibit return movement of the band in the distal direction.

Figure 24A:
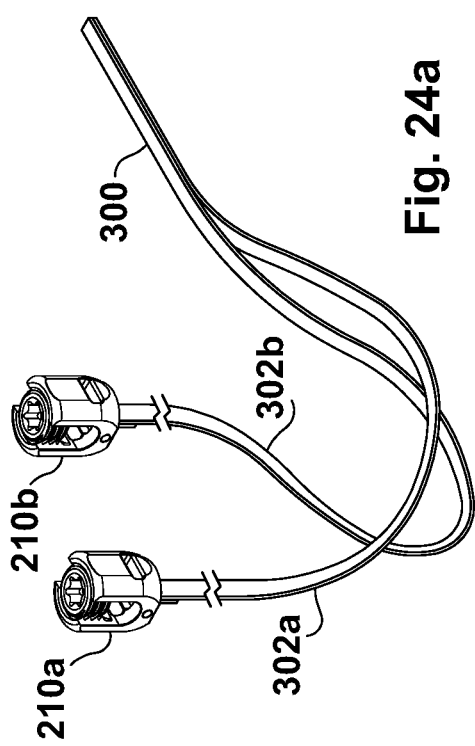
FIG. 24a is a perspective view of another embodiment of the invention, showing a dual tether band assembly.
Figure 24B:
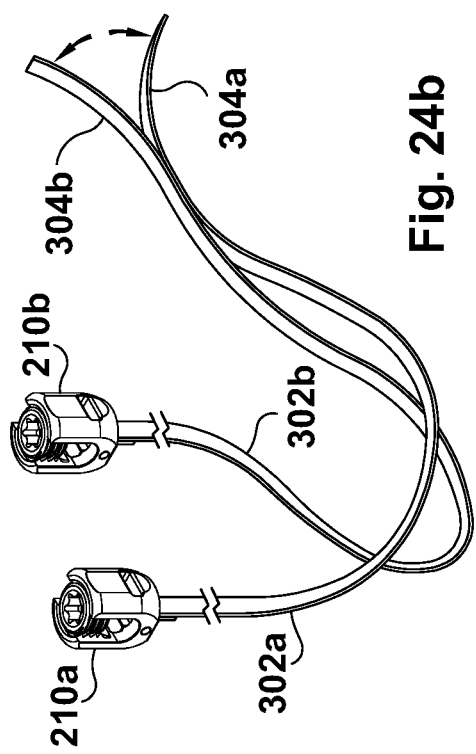
FIG. 24b is a perspective view of the clamp assembly of FIG. 24a, shown with a part of the dual tether band split into two individual bands.

The invention can be utilized in various applications and techniques. Several other embodiments of the invention and methods of use as illustrated in FIGS. 24a-32. A dual housing assembly is illustrated in FIGS. 24a-24b. The figures illustrate two housings 210a, 210b with a dual tether band 300 fixed to the bottom of each housing. The strands are connected to the housing as by the arrangement shown in FIG. 14, with the individual strands 302a, 302b of the band connected to a pin inserted through the housing. The proximal end of the band can be split in two ends 304a, 304b after being passed through a slot on another housing, or other device. After splitting and passing, each end 304a, 304b is secured independent of the other to each housing 210a, 210b, such as for example, under a surgical rod.

Figure 25:
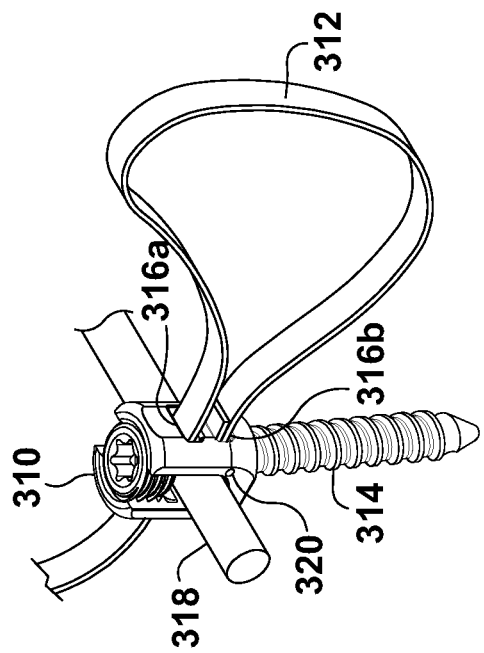
FIG. 25 is a perspective view of another embodiment of the invention, showing a tether band/pedicle screw assembly.
Figure 26:
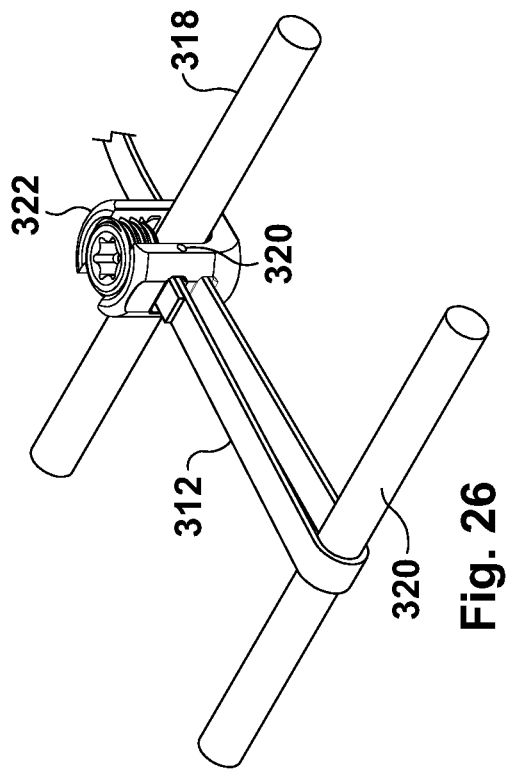
FIG. 26 is a perspective view of another embodiment of the invention, showing a tether band/cross-connector assembly.

Other embodiments of the invention can include housings having pedicle screw capability, such as for example, the housing illustrated in FIG. 25. The housing 310 includes a screw portion 314 having construction suitable for use as a pedicle screw. One or more slots allow for anchoring or passing of a tether band. As shown, a distal loop of a band 312 surrounds a mounting pin 320 and exits a lower slot 316b, and upon re-entry to the housing 310 passes through an upper slot 316a and over a surgical rod 318. This arrangement allows for additional fixation options, such as for example, to support resistance to screw pullout, e.g., in osteopenic bone. A similar arrangement is shown in FIG. 26, in which a band surrounds a second surgical rod 320. In this embodiment, the band is mounted to a surgical rod 320 and exits out an upper slot. In this arrangement with two surgical rods 318, 320, the assembly is used as a cross connector to add bi-lateral stability in rod/implant constructs.

Figure 27A:
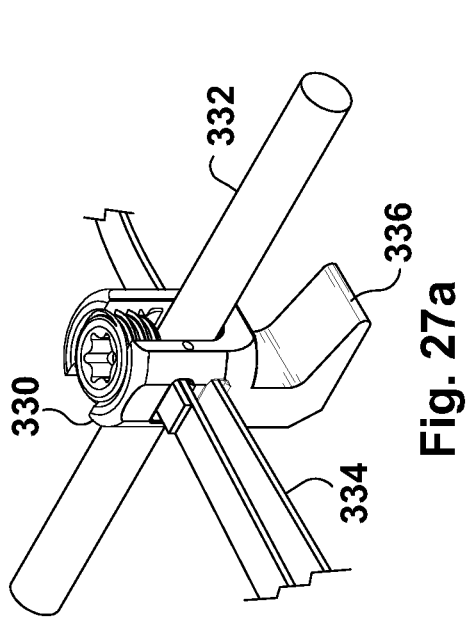
FIG. 27a is a perspective view of another embodiment of the invention, showing a tether band/hook assembly with the hook and the band in an opposite orientation.
Figure 27B:
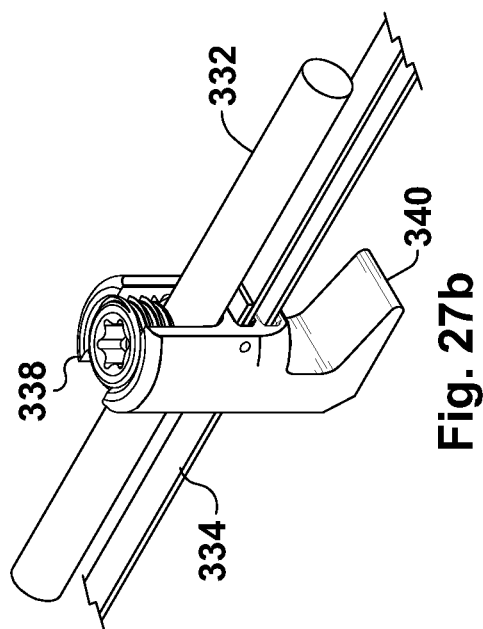
FIG. 27b is a perspective view of another embodiment of the invention, showing a tether band/hook assembly.

Other embodiments of the invention can include housings with laminar hooks used to engage bone. Specifically, the housing along the combination of hook, rods and tethers to prevent dislodging of hook, for example, to prevent proximal junctional kyphosis. FIGS. 27a and 27b illustrate housing 330, 338 with hooks 336, 340, respectively. In FIG. 27A, the rod 332 and tether 334 are positioned at opposing orientations, and with the tether above the rod. In contrast, the housing 338 of FIG. 27b positions the rod above the tether and at the same orientation, i.e., in a co-axial position. Other combinations of rod and tether positions can be practiced with this invention.

Figure 28:
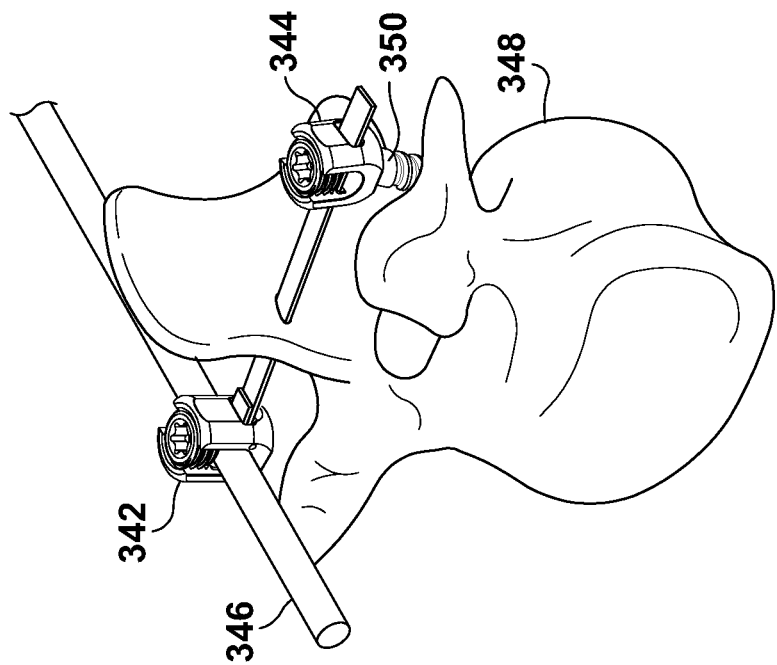
FIG. 28 is a perspective view of another embodiment of the invention, showing a two housing assembly and a transverse tether band.

Another exemplary assembly is shown in FIG. 28. As shown, a pedicle screw housing 344 is implanted into a vertebrae 348. A second housing is fixed to a rod 346 and positioned on an opposite side of the vertebrae 348 relative the pedicle screw housing 344. A tether band 350 stretches from a pin mounting in the housing 342, through a surgical created slot in the vertebrae, and to the pedicle screw housing 344. The use of tether band 350 in a transverse arrangement helps derotation of vertebral body and prohibits any creep of construct.

Figure 29:
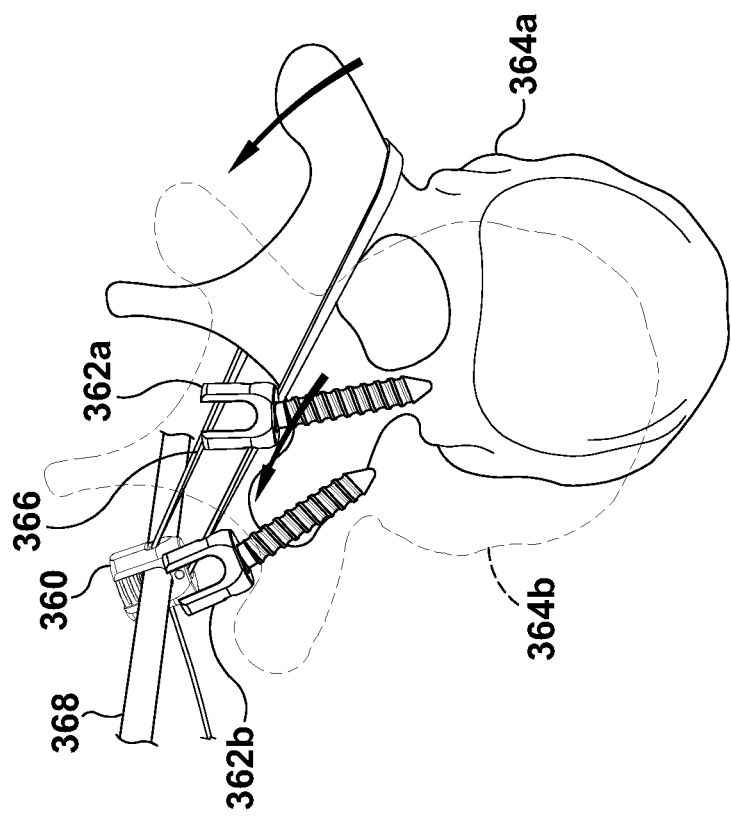
FIG. 29 is a perspective view of another embodiment of the invention, showing the installation of a tether band/pedicle screw assembly acting as a reduction device.

Multiple inventive housings and a tether band can also be advantageously used during surgery to help implant a rod. For example, FIG. 29 illustrates an exemplary use of a first housing, a pedicle screw housing, and a tether band 366 in which the tether band is used to laterally translate the pedicle screw housing to the implant rod. After the first housing 360 is mounted to a rod 368, the pedicle screw housing 362a (as shown in a first position) is translated to a second position 362b by use of the tether band 366, in effect moving the vertebrae (from a first position 364a to a second position 364b) to an position engageable with the rod 368.

Figure 30:
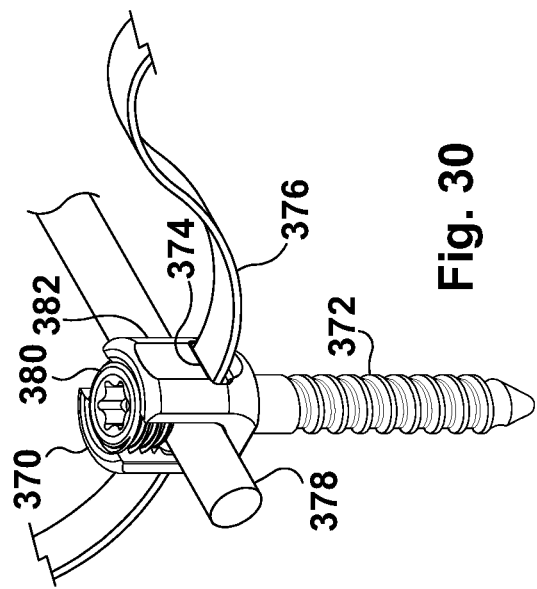
FIG. 30 is a perspective view of another embodiment of the invention, showing another tether/band/pedicle screw assembly.

As discussed, the inventive housing includes slots suitable for passing of a tether band. For example, pedicle screws with slots for tether band may be used to allow additional fixation options by accommodating passage of a tether band through the head of the screw. As shown in FIG. 30, a pedicle screw housing 370 includes a screw portion 372, and a head 382 having a slot 374 in each arm. A tether band 376 may pass above or below a surgical rod 378, and may be held in place by a set screw 380. Other examples using hooks 392 are illustrated in FIGS. 31a and 31b. These housings 394, 390 allow for additional fixation options by accommodating passage of a tether band 376 through the body of the housing transversely (as shown in FIG. 31a) or along the axis of the rod 378 (as shown in FIG. 31b). Other orientation combinations are possible in practice of invention.

Referring now to FIG. 32, a tether band and pedicle screw housing is shown in use in a reduction process. Specifically, a tether band 408 is used as a reduction device to seat a rod 404 into a pedicle screw housing 402. As shown, the housing is implanted into a vertebrae 400.

By use of tensioning instrument 406, the vertebrae 400 and pedicle screw housing 402 is moved in a direction $A_2$ to seat the rod in a desired position.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, software, hardware, control logic, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention.

Descriptions of exemplary methods or processes are not limited to inclusion of all steps as being required in all cases, nor is the order that the steps are presented to be construed as required or necessary unless expressly so stated.

The invention claimed is:

1. A clamp assembly for orthopedic stabilization, the assembly comprising:
   a unitary clamp housing having a top surface, a recess, and a distal base having a bottom surface, the recess defining a longitudinal axis and extending through the housing from the top surface through the distal base and toward the bottom surface, the housing further comprising one or more through slots, wherein at least one through slot is disposed at the bottom surface of the housing and any other of the one or more through slots is disposed at a surface of the housing selected from the bottom surface of the housing and a side surface of the housing;
   a securement assembly positionable within the recess in a co-axial relationship to a mating surface on the recess;
   a compression assembly comprising a compression element positionable within the distal base below and in contact in a co-axial relationship with the securement assembly; and
   a band sized for travel along a predetermined path defined in part by the at least one through slot in the housing, wherein a first end of the band is fixed to the clamp housing by securement of a looping portion of the first end around a pin or bridge disposed within the at least one through slot that is disposed at the bottom surface of the housing, the band being attached to itself to form the looping portion, and
   wherein the first end of the band is a starting point for travel of the band along the predetermined path and the band passes below the compression assembly and is compressible in the distal base when the securement assembly is positioned within the recess.

2. The clamp assembly of claim 1 wherein the mating surface of the recess comprises a locking feature for engaging with the securement assembly.

3. The clamp assembly of claim 2 wherein the locking feature on the mating surface of the recess comprises one or more of threads and a groove, and wherein the securement assembly comprises a securement element that is engageable with the mating surface of the recess.

4. The clamp assembly of claim 2 comprising more than two through slots, wherein at least two through slots are disposed opposite one another, each on the side surface of the housing and positioned on the housing to define the path of the band below the compression assembly.

5. The clamp assembly of claim 3 comprising more than two through slots, wherein at least two through slots are disposed opposite one another, each on the side surface of the housing and positioned on the housing to define the path of the band below the compression assembly.

6. The claim assembly of claim 5 wherein the side surface of the housing comprises first and second opposing elongate side arms that extend along the longitudinal axis defined by the recess, wherein each of the at least two through slots is disposed on the side surface of the housing in one of the opposing elongate side arms.

7. The claim assembly of claim 6 wherein the securement element is a surgical rod, and wherein the at least two opposing through slots in the elongate side arms define a band path below the surgical rod, and wherein the locking element is a set screw and at least a portion of the housing recess is threaded for engagement with the set screw.

8. The clamp assembly of claim 7, the clamp housing comprising on the bottom surface of the distal base two opposing coaxial holes and a pin insertable therein, the coaxial holes and inserted pin positioned to bisect the elongate slot aperture and form the starting point for travel of the band, and wherein a first end of the band is fixed to the clamp housing by engagement around the pin.

9. The clamp assembly of claim 7, the clamp housing comprising two elongate slot apertures on the bottom surface of the distal base and a solid bridge between the slot apertures, and wherein a first end of the band is fixed to the clamp housing by engagement through the two elongate slot apertures and secured to the bridge to form the starting point for travel of the band.

10. The clamp assembly of claim 1 comprising at least two through slots.

11. The clamp assembly of claim 1 wherein the clamp housing is unitary.

12. A clamp assembly for providing stabilization as a bone anchor, the assembly comprising:
- a unitary clamp housing comprising a recess, a top surface, a distal base and a bottom surface, and comprising two opposing arms extending from the base, the recess extending through the housing between the opposing arms and toward the bottom surface, the housing further comprising at least one through slot in each of the two opposing arms, and two slots disposed at the bottom surface of the housing in a parallel orientation to each other and separated by a bridge extending therebetween;
- a locking element positionable within the recess;
- a securement element comprising a surgical rod positionable within the recess below the locking element; and
- a band sized for travel along a predetermined path defined in part by the slots in the housing,
- wherein a first end of the band is fixed to the housing by securement of a looping portion of the first end around a pin or bridge disposed within a through slot disposed at the bottom surface, the band being attached to itself to form the looping portion,
- wherein the first end of the band is a starting point for travel of the band along the predetermined path, and
- wherein the slots in the arms are positioned on the housing to define the path of the band below the locking element.

13. A clamp assembly for orthopedic stabilization, the assembly comprising:
- a first unitary clamp housing having a first top surface, a first recess, and a first distal base having a first bottom surface, the first recess defining a first longitudinal axis and extending through the first unitary clamp housing from the first top surface through the first distal base and toward the first bottom surface, the first unitary clamp housing further comprising one or more first through slots, wherein at least one first through slot is disposed at the first bottom surface of the first unitary clamp housing and any other of the one or more first through slots is disposed on a first surface of the first unitary clamp housing selected from the first bottom surface of the first unitary clamp housing and a first side surface of the first unitary clamp housing;
- a first securement assembly positionable within the first recess in a first co-axial relationship to a first mating surface on the first recess; and
- a first compression assembly comprising a first compression element positionable within the first distal base below and in contact in a co-axial relationship with the first securement assembly;
- a second unitary clamp housing having a second top surface, a second recess, and a second distal base having a second bottom surface, the second recess defining a second longitudinal axis and extending through the second unitary clamp housing from the second top surface through the second distal base and toward the second bottom surface, the second unitary clamp housing further comprising one or more second through slots, wherein at least one second through slot is disposed at the second bottom surface of the second unitary clamp housing and any other of the one or more second through slots is disposed on a second surface of the second unitary clamp housing selected from the second bottom surface of the second unitary clamp housing and a second side surface of the second unitary clamp housing;
- a second securement assembly positionable within the second recess in a second co-axial relationship to a second mating surface on the second recess; and
- a second compression assembly comprising a second compression element positionable within the second distal base below and in contact in a co-axial relationship with the second securement assembly;
- a band having first and second ends and sized for travel along a predetermined path defined in part by one of the at least one first through slot and the at least one second through slot, the band being split at its first end into first and second strands that each terminate, respectively, in first and second strand ends,
- wherein the first strand of the first end of the band is fixed to the first unitary clamp housing by securement of a first looping portion formed in the first strand around a pin or bridge disposed within the at least one first through slot that is on the first bottom surface, the end of the first strand being attached to itself to form the first looping portion,
- wherein the second strand of the first end of the band is fixed to the second unitary clamp housing by securement of a second looping portion formed in the second strand around a pin or bridge disposed within the at least one second through slot that is on the second bottom surface, the end of the second strand being attached to itself to form the second looping portion, and
- wherein each of the first and second strands of the first end of the band are starting points for travel of the band along the predetermined path and wherein the second end of the band is passed along the predetermined path below at least one of the first and second recesses for the first and second compression assemblies and is compressible in the first and second distal bases when each of the first and second securement assemblies is respectively positioned in each of the first and second recesses in contact with each of the first and second compression assemblies.

14. The clamp assembly for orthopedic stabilization according to claim 13, wherein the first and second securement assemblies comprise a set screw, and the first and second compression assemblies comprise a spinal rod.

* * * * *